(12) United States Patent
Bengtsson et al.

(10) Patent No.: US 11,944,791 B2
(45) Date of Patent: Apr. 2, 2024

(54) MULTI-USE DRUG DELIVERY DEVICE FOR DRUGS WITH LESS PRESERVATIVES

(71) Applicant: Novo Nordisk A/S, Bagsvaerd (DK)

(72) Inventors: Henrik Bengtsson, Taastrup (DK); Vera Pinto Glenting, Copenhagen (DK); Joern Drustrup, Farum (DK); Jonas Kildegaard Pedersen, Vaerloese (DK)

(73) Assignee: Novo Nordisk A/S, Bagsvaerd (DK)

( * ) Notice: Subject to any disclaimer, the term of this patent is extended or adjusted under 35 U.S.C. 154(b) by 681 days.

(21) Appl. No.: 16/640,298

(22) PCT Filed: Aug. 20, 2018

(86) PCT No.: PCT/EP2018/072399
§ 371 (c)(1),
(2) Date: Feb. 19, 2020

(87) PCT Pub. No.: WO2019/042801
PCT Pub. Date: Mar. 7, 2019

(65) Prior Publication Data
US 2021/0077727 A1    Mar. 18, 2021

(30) Foreign Application Priority Data

Aug. 30, 2017 (EP) .................................... 17188590
Apr. 13, 2018 (EP) .................................... 18167233
May 7, 2018 (EP) .................................... 18170962

(51) Int. Cl.
*A61M 5/24* (2006.01)
*A61M 5/20* (2006.01)
(Continued)

(52) U.S. Cl.
CPC ............ *A61M 5/2459* (2013.01); *A61M 5/34* (2013.01); *A61M 39/24* (2013.01);
(Continued)

(58) Field of Classification Search
CPC .. A61M 2005/2474; A61M 2005/3206; A61M 5/2459; A61M 5/34; A61M 2005/3103; A61M 5/32; A61M 5/3293
See application file for complete search history.

(56) References Cited

U.S. PATENT DOCUMENTS 3,354,881 A    11/1967  Bloch
4,133,457 A    1/1979   Klassen
(Continued)

FOREIGN PATENT DOCUMENTS

CN    1744871 A    3/2006
CN    1764798 A    4/2006
(Continued)

OTHER PUBLICATIONS

Benitez, Zuleika and Robinson, Sage "Summer Tip: Insulin Storage" Jun. 2015 https://www.flushinghospital.org/newsletter/summer-tip-insulin-storage/ (Year: 2015).*

*Primary Examiner* — Bradley J Osinski
(74) *Attorney, Agent, or Firm* — Wesley Nicolas

(57) ABSTRACT

A multi-use drug delivery device for extended use, wherein the multi-use drug delivery device comprising a multi-use main portion (310) and a single-use flow conducting device (360) adapted for conducting drug to the subcutaneous tissue of a subject, wherein the change from a connected configuration to an unconnected configuration of the main portion and the flow conducting device is through the intermediate configuration. The intermediate configuration comprises an equalizing channel defining an equalizing flow path (304) different from an unintended flow path (303). The equalizing channel is adapted for equalizing the fluid pressure in a fluid communication volume (301) to the fluid pressure in the external environment, upon changing the configuration from the connected to the intermediate configuration and thereby expanding an internal volume, whereby an equalizing fluid (Continued)

flow along the equalizing flow path is larger than an unintended flow along the unintended flow path, whereby equalization of the fluid communication volume is provided with a reduced risk of introducing microorganisms from the flow channel (362) into the reservoir (311).

15 Claims, 15 Drawing Sheets

(51) Int. Cl.
*A61M 5/31* (2006.01)
*A61M 5/34* (2006.01)
*A61M 39/24* (2006.01)

(52) U.S. Cl.
CPC ........ *A61M 2005/2006* (2013.01); *A61M 2005/3103* (2013.01); *A61M 2005/3117* (2013.01); *A61M 2005/3123* (2013.01); *A61M 2005/3128* (2013.01)

(56) References Cited

U.S. PATENT DOCUMENTS

| | | | |
|---|---|---|---|
| 4,919,658 A | 4/1990 | Badia | |
| 5,340,359 A | 8/1994 | Segura Badia | |
| 6,871,838 B2 | 3/2005 | Raines et al. | |
| 7,291,133 B1 | 11/2007 | Kindler et al. | |
| 7,981,081 B2 | 7/2011 | Marsh et al. | |
| 8,066,692 B2 | 11/2011 | Simpson et al. | |
| 8,863,993 B2 | 10/2014 | Donnette et al. | |
| 8,863,998 B2 | 10/2014 | Painchaud et al. | |
| 9,241,828 B2 | 1/2016 | Pardes et al. | |
| 9,408,971 B2 | 8/2016 | Carlyon | |
| 10,105,492 B2 | 10/2018 | Simpson et al. | |
| 10,112,018 B2 | 10/2018 | Cowe | |
| 2004/0158204 A1 | 8/2004 | Reboul | |
| 2005/0043684 A1 | 2/2005 | Basta et al. | |
| 2005/0113750 A1 | 5/2005 | Targell | |
| 2008/0114295 A1* | 5/2008 | Glynn | A61M 5/24 604/110 |
| 2011/0168170 A1 | 7/2011 | Patton et al. | |
| 2011/0208128 A1 | 8/2011 | Wu et al. | |
| 2013/0018323 A1 | 1/2013 | Boyd et al. | |
| 2016/0001014 A1 | 1/2016 | Eilertsen et al. | |
| 2016/0008555 A1* | 1/2016 | Schraga | A61M 5/344 604/110 |
| 2020/0246547 A1 | 8/2020 | Glenting et al. | |
| 2021/0030966 A1 | 2/2021 | Bengtsson et al. | |

FOREIGN PATENT DOCUMENTS

| | | |
|---|---|---|
| CN | 2910250 Y | 6/2007 |
| CN | 104703640 A | 6/2015 |
| CN | 102844073 | 11/2015 |
| EP | 0716860 A3 | 11/1996 |
| EP | 0795342 A2 | 9/1997 |
| EP | 1948523 A1 | 7/2008 |
| EP | 2704773 A1 | 3/2014 |
| GB | 706150 A | 3/1954 |
| GB | 739753 A | 11/1955 |
| JP | 2007516785 A | 6/2007 |
| WO | 2007056233 A1 | 5/2007 |
| WO | 2012152703 A1 | 11/2012 |
| WO | 2013112486 A1 | 8/2013 |
| WO | 2014009444 A1 | 1/2014 |
| WO | 2014064100 A1 | 5/2014 |
| WO | 2014125067 A1 | 8/2014 |
| WO | 2015155229 A1 | 10/2015 |
| WO | 2015173151 A1 | 11/2015 |
| WO | 2015177082 | 11/2015 |
| WO | 2016061062 A1 | 4/2016 |
| WO | 2016131954 A1 | 8/2016 |
| WO | 2017032599 A1 | 3/2017 |
| WO | 2017050694 | 3/2017 |
| WO | 2017129314 | 8/2017 |
| WO | 2018085952 | 5/2018 |

* cited by examiner

⇑ Movement

⇑ Air flow

⇑ Movement

⇑ Air flow

MULTI-USE DRUG DELIVERY DEVICE FOR DRUGS WITH LESS PRESERVATIVES

CROSS-REFERENCE TO RELATED APPLICATIONS

This application is a 35 U.S.C. § 371 National Stage application of International Application PCT/EP2018/072399 (published as WO 2019/042801), filed Aug. 20, 2018, which claims priority to European Patent Applications 17188590.8, filed Aug. 30, 2017, 18167233.8, filed Apr. 13, 2018, and 18170962.7, filed May 7, 2018, the contents of all above-named applications are incorporated herein by reference.

TECHNICAL FIELD

The present invention relates to a multi-use drug delivery device for extended use, wherein the multi-use drug delivery device comprises a multi-use main portion and a single-use flow conducting device adapted for conducting drug to the subcutaneous tissue of a subject, wherein the main portion of the drug delivery device comprises a drug reservoir, wherein the reservoir comprises multiple doses of a liquid drug formulation, and wherein the drug formulation allows microbial growth upon introduction of microorganisms into the reservoir during extended use, i.e, the drug formulation comprise less preservatives and the concentration is insufficient to inhibit microbial growth upon unintended introduction. The invention further relates to a method of removing the single-use flow conducting device from the main portion of the multi-use drug delivery device, comprising preventing introducing microorganisms into the reservoir during removal.

BACKGROUND OF THE INVENTION

In the disclosure of the present invention reference is mostly made to the treatment of diabetes by delivery of liquid insulin formulation, however, this is only an exemplary use of the present invention.

Drug delivery devices in the form of drug injection devices have greatly improved the lives of patients who must self-administer liquid drugs and biological agents. Drug injection devices may take many forms, including simple disposable devices that are little more than an ampoule with an injection means or they may be highly sophisticated electronically controlled instruments with numerous functions. Some devices are intended for single-use and may come with an integrated needle, e.g. comprising a so-called pre-filled syringe. However, in case the drug delivery device is intended to be used for multiple injections, it will typically be designed for use with a replaceable needle or cannula unit which ideally is to be replaced for each injection of a dose of drug. Regardless of their form, they have proven to be great aids in assisting patients to self-administer injectable drugs and biological agents. They also greatly assist care givers in administering injectable medicines to those incapable of performing self-injections.

In particular pen-style injection devices have proven to provide an accurate, convenient, and often discrete, way to administer drugs and biological agents, such as insulin. While pen-style injection devices are typically cylindrically shaped with a mounted needle protruding from the most distal portion of one end of the device, some devices have other shapes with the needle no longer protruding from the most distal part of an end of the device, e.g. Innovo® and InnoLet® from Novo Nordisk A/S, Bagsvaerd, Denmark.

Typically, injection devices use a pre-filled cartridge containing the liquid medication of interest, e.g. 1.5 or 3.0 ml of insulin or growth hormone formulation. The cartridge is typically in the form of a generally cylindrical transparent glass cylinder having a distal bottle neck portion with a distal opening closed by a needle pierceable septum and an opposed proximal opening in which an elastomeric piston is received, the piston being arranged to be moved by the dosing mechanism of the injection device. The injection devices generally are of two types: "Durable" devices and "disposable" devices. A durable device is designed to allow a user to replace one cartridge with another cartridge, typically a new cartridge in place of an empty cartridge. In contrast, a disposable device is provided with an integrated cartridge which cannot be replaced by the user; when the cartridge is empty the entire device is discarded.

As described above, a drug delivery device intended to be used for multiple injections is typically designed to be used in combination with a replaceable needle unit comprising a proximal needle portion adapted to be inserted into the drug-filled cartridge through a needle-penetrable septum seal and a distal needle portion adapted to be introduced subcutaneously, this allowing a given dose amount of liquid drug formulation to be injected subcutaneously through the hollow needle. Since the proximal needle portion penetrates the seal of the cannula and provides a flow path from the inside of the cannula to the outside, a risk of contamination of the cartridge contents is introduced.

Drug delivery devices can also be in the form of infusion systems comprising a pump with the above mentioned cartridge, and an infusion set conducting liquid drug from the reservoir of the cartridge to an infusion site on a subject.

The risk of contamination is primarily related to removal of the needle unit or the infusion set after use. As long as the cannula is penetrating the cartridge seal, it provides access from surroundings to the drug formulation and should thus be removed immediately after injection. However, after injection but prior to removal of the needle, the small volume of drug formulation inside the needle itself may be contaminated either from body fluids or from bacteria in the surroundings when the cannula is extracted from the skin of the subject. When the cannula is removed from the cartridge, some of the remaining fluid in the cannula may be sucked into the cartridge, thereby contaminating the drug formulation in the cartridge.

Therefore, drug formulations for use in multi dose injection devices must contain a sufficient level of preservatives to insure biostatic conditions during the expected in-use time of the cartridge to counter such contamination, i.e., to ensure conditions wherein growth of microorganisms are inhibited. This requirement is included in chapters on injectable drug formulations in current versions of international pharmacopeia.

The different national and international pharmacopoeias are issued by officially recognized authorities and provide common quality standards throughout the pharmaceutical industry. The standards for product quality tests of parenteral drug products, which include injections, is a part of the pharmacopoeia and some of the requirements are described in the following. Parenteral drug products are injected through the skin or other external boundary tissue, to allow the direct administration of the active drug substance(s) into blood vessels, organs, tissues, or lesions. Injections may exist as either immediate- or extended-release dosage forms. Routes of administration for parenteral drug products include intravenous, intraventricular, intra-arterial, intra-articular, intramuscular, intrathecal, intracisternal, intraocular and subcutaneous. Parenteral dosage forms include solutions, suspensions, emulsions, sterile powders for solutions and suspensions (including liposomes), and products that consist of both a drug and a device such as drug-eluting stents.

A regulatory requirement to drug delivery devices is that the packaging system should not interact physically or chemically with the preparation to alter its strength, quality, or purity beyond the official or established requirements. The packaging system should be closed or sealed in such a manner as to prevent contamination or loss of contents. Validation of container integrity must demonstrate no penetration of microbial contamination or gain or loss of any chemical or physical parameter deemed necessary to protect the product.

The above mentioned drug delivery devices are more than just a packaging system, as they have additional functions to ease administration. Such drug delivery devices may be referred to as dual function container-closure systems.

According to the pharmacopoeias, dual function container-closure systems are characterized by the addition of one or more intended functions to that of a container and require special consideration for integrity evaluation. Frequently, one compartment of the dual container-closure system, a container compartment, is designed to contain the drug or solution prior to use or activation. Another compartment, a delivery compartment, different in function and design, either directly delivers the product from the system-product containment compartment to a fluid pathway for direct injection of the patient or communicates with a sterile pathway of another access device. For example, a prefilled syringe contains a solution (the container compartment) and a device component (the delivery compartment) physically separated from the container compartment and used to directly administer the drug to the patient.

Therefore, dual container-closure systems typically have at least two compartments that require microbial barrier properties, and packaging integrity after sterilization and/or aseptic filling should be demonstrated for both compartments. In many cases, different portions of the dual system require different integrity testing methods. The selection of the integrity testing method is determined primarily on the basis of the intended objectives or performance requirements of the particular compartment. For example, the solution or drug-containing container compartment of the dual container-closure system must be enclosed or sealed in a manner that precludes leakage of product or microbial ingress during and following the manufacturing process. On the other hand, the delivery portion (the portion comprising the delivery compartment) of the dual container-closure system frequently contains a fluid pathway that is empty during the sterilization or aseptic filling process and is intended to remain dry until the product container portion is activated prior to use. A covering, a sheath, or perhaps a cap designed to vent during sterilization and storage protects the delivery compartment from airborne microbial ingress throughout the life of the article. However, this portion of the device is frequently not designed to prevent liquid ingress. Liquid ingress can be precluded by secondary packaging or by the physical design of the system itself.

Closures for multiple-dose containers permit the withdrawal of the contents without removal or destruction of the closure. The closure permits penetration by a needle and, upon withdrawal of the needle, closes at once, protecting the container against contamination. Validation of the multiple-dose container integrity must include verification that such a package prevents microbial contamination or loss of product contents under anticipated conditions of multiple entry and use.

For example, for testing prefilled syringes without attached sterile needles, the test includes expelling and transferring the content to a culture medium. At intervals during the incubation period and at its conclusion, examine the media for macroscopic evidence of microbial growth. If no evidence of microbial growth is found, the product to be examined complies with the test for sterility In multiple-dose containers the liquid drug is preserved with preservatives in order to prevent microbial growth during the extended use, i.e., small doses over an extended in-use time as in continuous delivery or larger doses over an extended in-use time. The use of preservatives may in some cases reduce the efficacy of the drug and in some cases be incompatible with the drug, which means that such type of drug formulations cannot be used with a multi-dose injection device. For example, the necessary preservatives would destroy the drug substance in the cartridge by precipitating the drug substance or chemically react with it.

WO 2015/1770821 discloses a medical cartridge for multiple doses of a medical drug, which allows the waste of medical drug to be minimised, without requiring the use of preservatives in the medical drug. The medical cartridge is provided with a one way valve, arranged in an interior part 5 of the medical cartridge at a position near an outlet end. The one way valve is arranged to allow a fluid flow from the interior of the medical cartridge towards the outlet end, and to prevent a fluid flow from the outlet end towards the interior of the medical cartridge. An injection needle can be mounted via a needle adapter at the outlet end of the cartridge, and extends through a septum, at the outlet end of the cartridge. It is an advantage that the one way valve is arranged in an interior part of the cartridge, because thereby the one way valve can be designed in a manner which reduces a dead volume inside the cartridge. By arranging the one way valve in the interior part of the cartridge, no additional or exterior interface between the outlet end of the cartridge and the one way valve is required, and thereby the risk of leaks at such an interface is eliminated, or at least considerably reduced. The description of a different embodiment indicates that the one way valve may replace a passive septum of the medical cartridge. According to such an embodiment, the one way valve is arranged inside the cartridge, immediately adjacent to the outlet end, and in immediate contact with an injection needle connected to the outlet end of the cartridge. This design may even further reduce the dead volume inside the cartridge, thereby even further reducing the waste of medical drug.

For such systems it is important that there is no introduction of microorganisms during use, which includes the handling steps in connecting and removing a needle unit from the drug delivery device multiple times during the extended use period.

DISCLOSURE OF THE INVENTION

In the disclosure of the present invention, embodiments and aspects will be described which will address one or more of the above objects or which will address objects apparent from the below disclosure as well as from the description of exemplary embodiments.

Thus, in a general aspect of the invention is provided a multi-use drug delivery device for extended use, wherein the multi-use drug delivery device comprises a multi-use main portion comprising a central axis (A) defining a longitudinal direction and a single-use flow conducting device adapted for conducting drug to the subcutaneous tissue of a subject, wherein the drug delivery device is adapted to enable the flow conducting device to be movably arranged relative to the main portion, wherein the relative movement can be guided by cooperating structures of the main portion and the flow conducting device, wherein the drug delivery device is configurable in:
  a connected configuration, wherein the flow conducting device is arranged in a connected position relative to the main portion, wherein the relative movement is guided, and wherein the relative position defines a first distance (d1) in the longitudinal direction between the flow conducting device and the main portion, wherein the relative position corresponds to a first internal volume confined by an outer surface of the drug delivery device,
  an intermediate configuration, wherein the flow conducting device is movably arranged in an intermediate position relative to the main portion, wherein the relative movement is guided, and wherein the relative position defines a second distance (d2) in the longitudinal direction between the flow conducting device and the main portion, which is larger than the first distance (d1), wherein the relative position corresponds to a second internal volume confined by an outer surface of the drug delivery device,
  an unconnected configuration, wherein the flow conducting device is arranged in an unconnected position relative to the main portion, wherein the relative movement is not guided, and thereby the main portion and the flow conducting device are not connected, and
  wherein a change of configuration of the drug delivery device is adapted to be provided by a movement of the flow conducting device in the longitudinal direction relative to the main portion, wherein the change from the connected configuration to the unconnected configuration is through the intermediate configuration,
  wherein the second internal volume is larger than the first internal volume, and whereby the internal volume confined by the outer surface of the drug delivery device expands, in response to changing the drug delivery device from the connected configuration to the intermediate configuration,
  wherein the main portion of the drug delivery device comprises a drug reservoir, a drug expelling mechanism for pressurizing the reservoir and thereby expelling an amount of drug, wherein the reservoir comprises multiple doses of a liquid drug formulation, and wherein the drug formulation allows microbial growth upon introduction of microorganisms into the reservoir during extended use,
  wherein the main portion further comprises a drug outlet and an outlet surface, wherein the outlet surface provides a portion of an outer surface of the main portion, and
  wherein the flow conducting device comprises a flow channel comprising a channel inlet and a channel outlet, wherein the flow channel is adapted for forming a combined flow path with the drug outlet,
  wherein the flow conducting device further comprises an inlet surface for interfacing the outlet surface of the main portion,
  wherein the drug delivery device further defines a fluid communication volume being a fluid or gaseous volume at the channel inlet, and an unintended flow path from the channel outlet through the flow channel and to the fluid communication volume, and
  wherein the connected configuration further comprises, the outlet surface is interfacing the inlet surface, and wherein the drug outlet is arranged in the outlet surface to allow the drug to flow from the main portion to the flow conducting device along the combined flow path, in response to the pressure in the reservoir exceeds a pressure threshold, and wherein the fluid communication volume provides a portion of the combined flow path and the first internal volume of the drug delivery device, and
  wherein the unconnected configuration further comprises, the outlet surface is exposed to the external environment, the drug outlet is arranged in a closed state, and wherein the drug outlet is arranged to inhibit the introduction of microorganisms from the external environment and into the reservoir,
  wherein the intermediate configuration further comprises an equalizing channel defining an equalizing flow path different from the unintended flow path, wherein the equalizing channel defining the equalizing flow path is adapted for equalizing the fluid pressure in the fluid communication volume to the fluid pressure at the channel outlet, upon changing the configuration from the connected to the intermediate configuration and thereby expanding the internal volume, whereby an equalizing fluid flow along the equalizing flow path is larger than an unintended flow along the unintended flow path, whereby equalization of the fluid communication volume is provided with a reduced risk of introducing microorganisms from the flow channel into the reservoir.

In a further aspect is provided a multi-use drug delivery device, wherein the equalizing flow path is defined as a flow path from an equalizing inlet in fluid communication with the external environment, along the outlet surface and to the fluid communication volume, and wherein the intermediate configuration further comprises the equalizing inlet is adapted to be in equilibrium with the channel outlet.

In a further aspect is provided a multi-use drug delivery device, wherein the outlet surface of the main portion further comprises a first sealing portion, and wherein the inlet surface of the flow conducting device further comprises a second sealing portion adapted to provide a pressure seal with the first sealing portion, in response to the establishment of a compression force between the two sealing portions, wherein the pressure seal provides a portion of the combined flow path established in the connected configuration.

In a further aspect is provided a multi-use drug delivery device, wherein the connected configuration further comprises the pressure seal is adapted to sustain an internal fluid pressure in the combined channel, wherein the intermediate configuration further comprises the pressure seal is broken and provides a portion of the equalizing flow path defined from the external environment to the fluid communication volume.

In a further aspect is provided a multi-use drug delivery device, wherein the channel seal provides a radially extending interface between the first sealing portion and the second sealing portion, wherein the channel seal can be established by moving the main portion and the flow conducting device into contact in the longitudinal direction, wherein the compression force can be increases continuously in response to movement after contact, and wherein the gradient of the compression force is continuously increasing, and wherein the radial direction is normal to the longitudinal direction.

In a further aspect is provided a multi-use drug delivery device, wherein the channel seal provides a longitudinally extending interface between the first sealing portion and the second sealing portion, wherein the channel seal can be established by moving the main portion and the flow conducting device into contact in the longitudinal direction, wherein the compression force is substantially constant in response to continued movement during contact, and wherein the radial direction is normal to the longitudinal direction.

In a further aspect is provided a multi-use drug delivery device, wherein the main portion further comprises a movable valve member, wherein the movable valve member is adapted for being movable in the longitudinal direction between a normally closed position, wherein the valve member closes the channel outlet, and a retracted open position, wherein the combined flow path can be established, and wherein the valve member is adapted to be biased towards the normally closed configuration, wherein the connected configuration further comprises the valve member being in the retracted open position, wherein the intermediate configuration further comprises, the valve member being in an intermediate position between the retracted open position and the normally closed position, wherein the fluid communication volume is confined between the inlet surface and the outlet surface within a constant volume, and whereby the fluid communication volume is adapted to be substantially constant during a change between the connected and the intermediate configuration.

In a further aspect is provided a multi-use drug delivery device, wherein the connected configuration further comprises a gas filled state and a fluid-filled state, wherein the gas-filled state comprises the flow channel s filled with air, and wherein the fluid-filled state comprises the flow channel is partly filled with the fluid drug, and defines a first flow resistance for fluid flowing in the equalizing flow path, wherein the equalizing flow path from the external environment define a second flow resistance for gas flowing from the external environment to the fluid communication volume, wherein the second flow resistance is smaller than the first flow resistance, whereby gas will flow along the equalizing flow path will be larger than the fluid flow along the second flow path, in response to a pressure drop in the fluid communication volume.

In a further aspect is provided a multi-use drug delivery device, wherein the main portion comprises a first connector, wherein the flow conducting device comprises a second connector, wherein the first and second connector are adapted to engage with each and provide the guided relative movement between the connected and the intermediate configuration.

In a further aspect is provided a multi-use drug delivery device, wherein the main portion is provided with a normally closed valve contributing to the pressure threshold.

In a further aspect is provided a multi-use drug delivery device, wherein the channel outlet is provided with a normally closed valve (1030C) contributing to the pressure threshold.

In a further aspect is provided a multi-use drug delivery device, wherein the channel outlet is closed by a septum in the unconnected configuration.

In a further aspect is provided, a method of removing a single-use flow conducting device from a main portion of a multi-use drug delivery device in the described aspects, wherein the method comprises:

providing a multi-use drug delivery device in the connected configuration in a fluid-filled state, wherein the flow channel is partly filled with the drug from the reservoir, removing the flow conducting device by moving the flow conducting device relative to the main portion and thereby changing the configuration of the drug delivery device from the connected to the unconnected configuration via the intermediate configuration, and thereby expanding the internal volume, and providing an equalizing fluid flow along the equalizing flow path, which is larger than an unintended flow along the unintended flow path, and thereby preventing a flow along the unintended flow path, and reducing the risk of introducing microorganisms from the flow channel and into the reservoir.

BRIEF DESCRIPTION OF THE DRAWINGS

In the following embodiments of the invention will be described with reference to the drawings:

FIG. 13C illustrate the unconnected configuration.

In the figures like structures are mainly identified by like reference numerals.

DESCRIPTION OF EXEMPLARY EMBODIMENTS

Figure 1A:
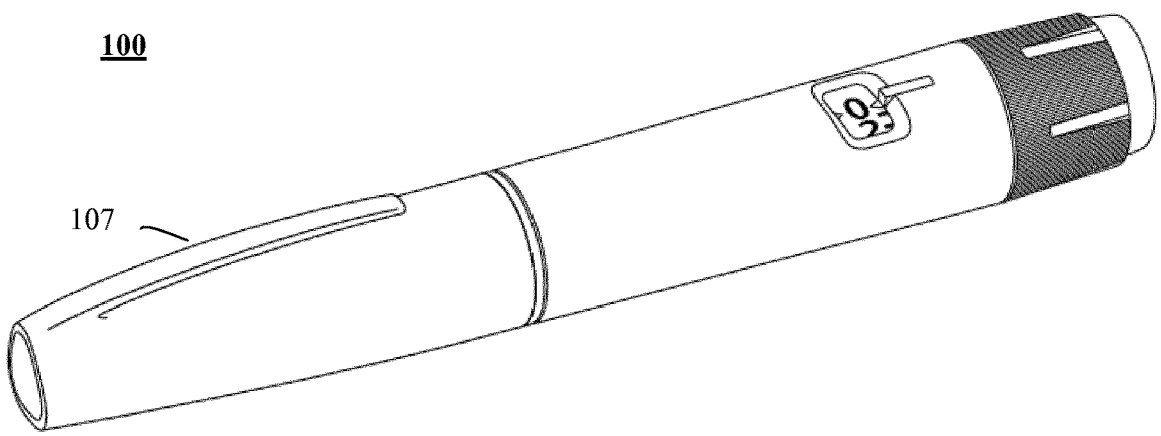
FIGS. 1A, 1B show an example of a drug delivery device in the form of an injection device. The injection device is shown with and without a protecting cap.

When in the following terms such as "upper" and "lower", "right" and "left", "horizontal" and "vertical" or similar relative expressions are used, these only refer to the appended figures and not necessarily to an actual situation of use. The shown figures are schematic representations for which reason the configuration of the different structures as well as their relative dimensions are intended to serve illustrative purposes only. When the term member is used for a given component it can be used to define a unitary component or a portion of a component, having a one or more functions.

Before turning to embodiments of the present invention per se, an example of an automatic drug delivery device in the form of an automatic injection device for multiple injection, and a drug delivery device in the form of continuous infusion device will be described. The described drug delivery devices provide the basis for the exemplary embodiments of the present invention.

The automatic drug delivery device is a prior art resettable dial-up/dial down automatic drug delivery device will be described. The pen device 100 comprises a cap part 107 and a main part having a proximal body or drive assembly portion with a housing 101 in which a drug expelling mechanism is arranged or integrated, and a distal cartridge holder portion 110 in which a drug-filled transparent cartridge 120 with a distal needle-penetrable septum is arranged and retained in place by a cartridge holder attached to the proximal portion, the cartridge holder having a pair of opposed openings 111 allowing a portion of the cartridge to be inspected. Distal coupling means 115 allows a needle assembly to be releasably mounted in fluid communication with the cartridge interior. The cartridge is provided with a piston driven by a piston rod forming part of the expelling mechanism and may for example contain an insulin, GLP-1 or growth hormone formulation. A proximal-most rotatable dose setting member 140 serves to manually set a desired dose of drug shown in display window 102 and which can then be expelled when the button 190 is actuated. Depending on the type of expelling mechanism embodied in the drug delivery device, the expelling mechanism may comprise a torsion spring as in the shown embodiment which is strained during dose setting and then released to drive the piston rod when the release button is actuated. More specifically, during dose setting a drive member to which the spring is connected is rotated to a rotational position corresponding to the set dose, the drive member thereby being in an energized state. A scale drum with dose size numerals is coupled to the drive member such that the size of the currently set dose is shown in the display window, e.g. by means of a threaded connection with the housing. To prevent the drive member from rotating the dose setting mechanism is provided with a holding mechanism, which in the exemplary embodiment is in the form of a ratchet mechanism (not shown on figure). When the user desires to expel the set dose the button is actuated whereby the drive member is brought into engagement with the piston rod drive mechanism and the holding mechanism subsequently released.

Figure 1B:
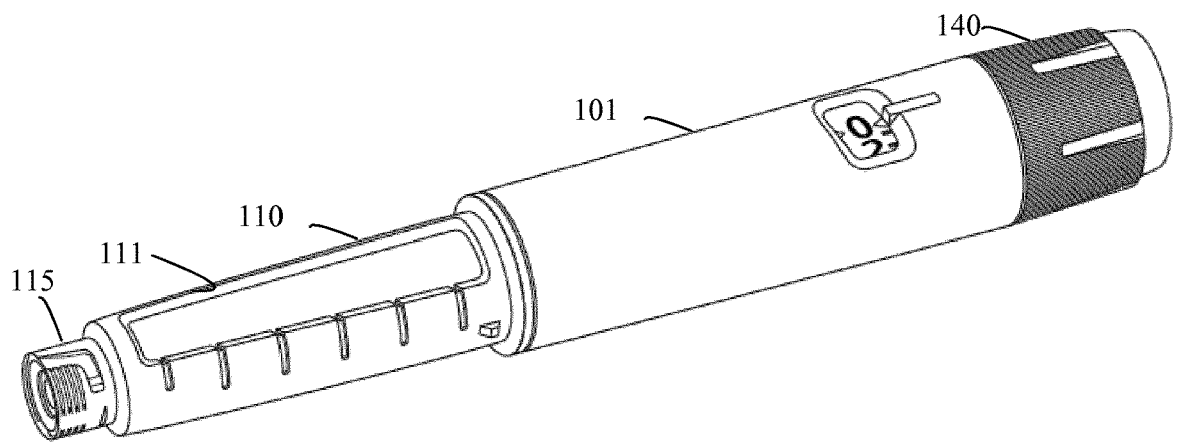
Figure 1C:
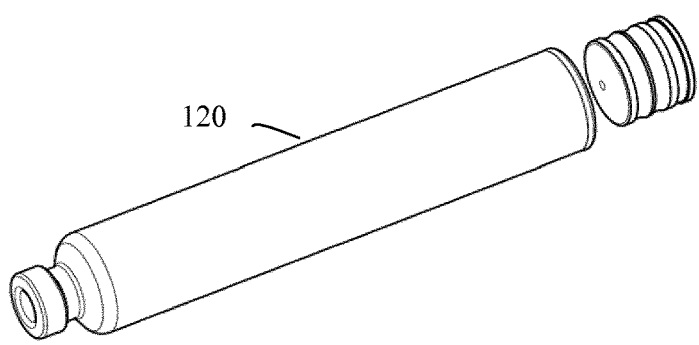
FIG. 1C shows a pressurizable drug reservoir in the form of a cartridge, which can be inserted into the drug delivery device shown in FIGS. 1A and 1B

Although FIGS. 1A, 1B and 1C show a drug delivery device of the pre-filled type, i.e. it is supplied with a pre-mounted cartridge and is to be discarded when the cartridge has been emptied, in alternative embodiments the drug delivery device may be a durable device designed to allow a cartridge assembly to be replaced, e.g. in the form of a cartridge assembly comprising a cartridge mounted in a cartridge holder. Such an assembly may further be provided with a pre-mounted piston rod.

Figure 1D:
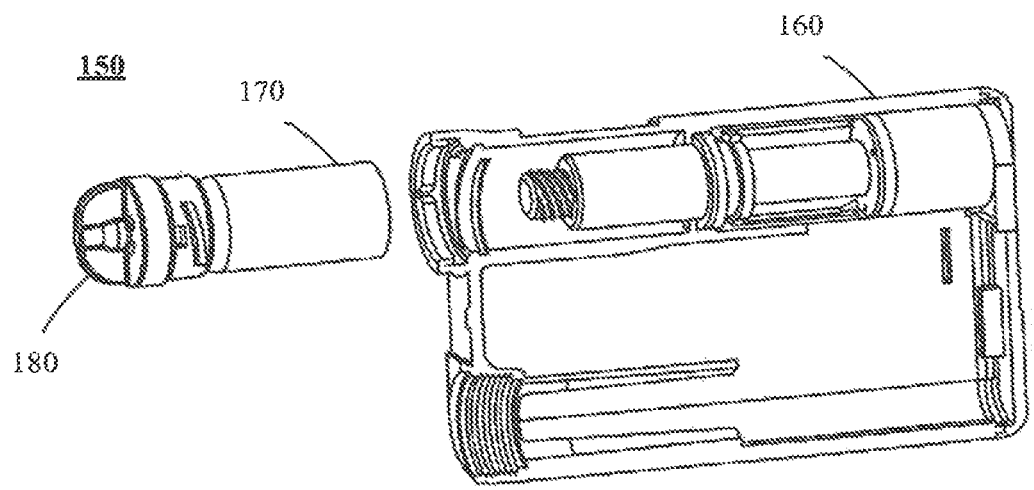
FIG. 1D shows an example of a drug delivery device in the form of an infusion pump. The drug delivery device is shown with a pump cartridge which is to be inserted into the drug delivery device.
Figure 1E:
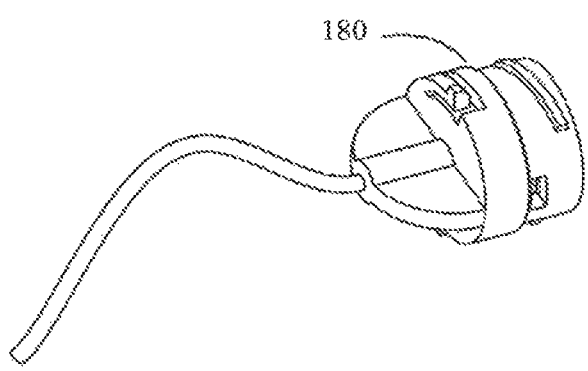
FIG. 1E shows an infusion set which can be used in combination with embodiments of the present disclosure.

FIG. 1D shows a drug delivery device 150 in the form of a continuous infusion pump, as disclosed by Medtronic Minimed in U.S. Pat. No. 6,248,093. The figure shows a pump housing 160, a pump cartridge 170, and a hub 180 for an infusion set. FIG. 1E shows an infusion set with a hub 180, which can be used in embodiments of the present disclosure.

Preservatives are normally needed to prevent microbial or bacterial growth in drug formulations for extended or multiple use. In products from Novo Nordisk A/S, one or both of the preservatives phenol and m-cresol are used to ensure that minor microbial contaminations will not grow during the expected lifetime of a multi dosed injectable. However, phenol and m-cresol are toxic (which is required for them to work as intended) and may therefore as a side effect cause injection site reactions, or in some cases allergic reactions. This also means that additional restrictions applies to the selection of new protein/peptide drugs, since they are required to be preservative stabile, especially when the drug product is intended for daily or weekly use. Thus, it would in some cases be preferred to be able to reduce or omit the addition of preservatives to a given drug. It should be noted that substances that are regarded as preservatives may be added in lower amounts with the purpose of acting as stabilizer of the drug substance, e.g., insulin substances.

To ensure antimicrobial requirements can be met without adding preservatives to the drug itself, two major issues must be addressed. Firstly, it must be ensured that a contaminated needle or cannula cannot be inserted in the cartridge and introduce microbial contamination of the cartridge. Secondly, it must be ensured that backflow through the cannula is not possible which would introduce a risk of microbial contamination through backflow of body fluids from the user. This concept should not be confused with known arrangements in which preservative-filled reservoirs are provided to allow a subcutaneous needle to safely be used more than once, e.g. as disclosed in U.S. Pat. No. 3,354,881 and WO 2014/064100.

Figure 2A:
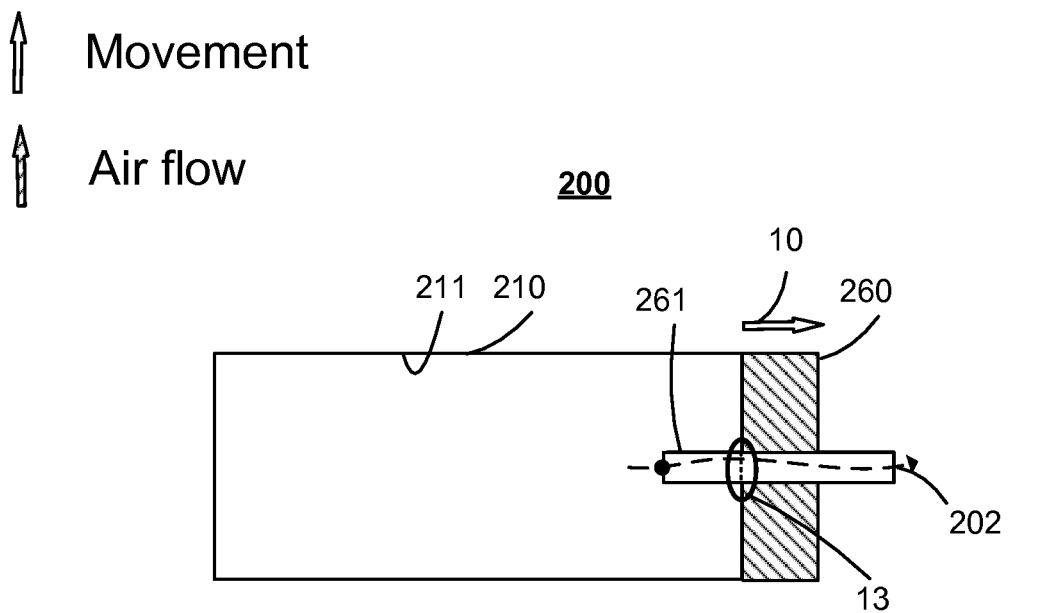
FIGS. 2A-2C illustrate schematically a prior art drug delivery device during removal of a flow conducting device from a main portion of the prior art drug delivery device, wherein a fluid contained in the flow conducting device can be sucked into the main portion.
Figure 2B:
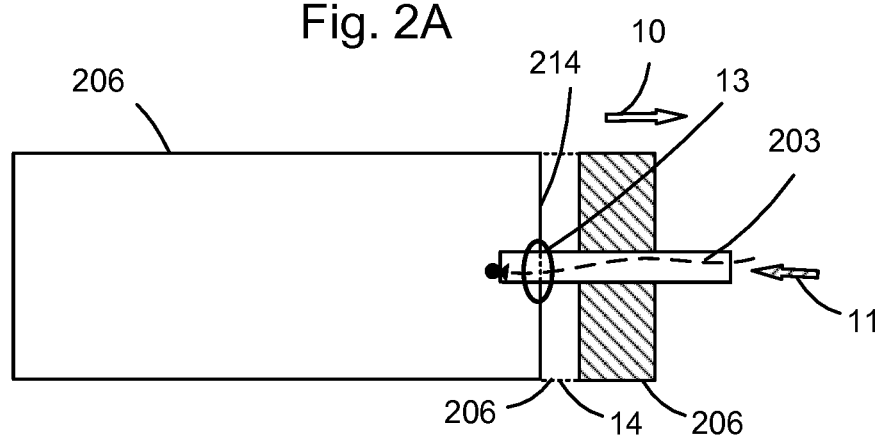
Figure 2C:
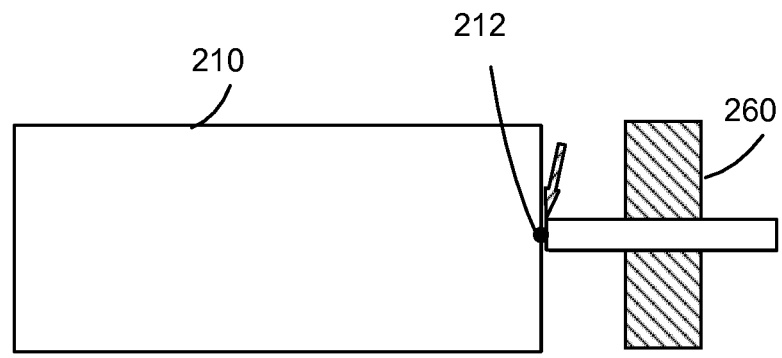

FIGS. 2A-2C illustrate schematically a prior art drug delivery device 200 during removal of a single-use flow conducting device 260 from a multi-use main portion 260, wherein a fluid contained in the flow conducting device 260 can be sucked into the main portion. FIGS. 2A-2C thereby illustrate the problem that arises, if prior art technology is used for administrating drugs allowing microbial growth upon unintended introduction of microorganisms.

FIG. 2A shows the drug delivery device in a connected configuration, wherein the main portion 210 comprising a septum 214 is pierced by a proximal piercing needle 261 of the flow conducting device. Hereby, a fluid tight seal is established between the septum 214 and the proximal piercing needle 261, with the proximal piercing needle extending into a reservoir 211 containing the drug. The area wherein the seal is formed is indicated by the solid ring 13, and the dashed arrow 202 illustrates that a combined flow path 202 can be established in the connected configuration. FIG. 2A also illustrates the unset of a relative movement between the flow conducting device and the main portion, the mechanical movement is illustrated by the white arrow 10.

FIG. 2B illustrates an intermediate state, wherein the main portion and the flow conducting device have been separated in the longitudinal direction. The half-half dashed line 14 illustrate that the main portion is guided relative to flow conducting device, wherein the guided movement can be obtained by the proximal piercing needle 261 sliding in the hole formed in the septum 214, or by connectors between the main portion and the flow conducting device. During the guided movement from the connected configuration in FIG. 2A to the intermediate configuration in FIG. 2B the internal volume of the drug delivery device expands. The internal volume is confined by the outer surface 206. During the guided movement, the proximal piercing needle is withdrawn from the reservoir, whereby the reservoir volume expands and the pressure in the reservoir will consequently decrease. To equalize the pressure drop with the ambient pressure, a flow of air, indicated with hatched arrow 11, will be induced from an outlet of the flow conducting device 260 to the inlet, whereby fluid in the flow conducting device will flow along the unintended flow path 203, and may introduce unintended introduction of microorganisms.

FIG. 2C illustrates the drug delivery device in an unconnected configuration, wherein there is no connection or guidance between the main portion and the flow conducting device. As the inlet of the flow conducting device is completely withdrawn from the septum, air will flow to the inlet end, if there still remains a small under pressure. However, this situation will only arise if the flow conducting device 230 is blocked during removal.

With reference to FIGS. 3-9 exemplary embodiments of the drug delivery system 300, 400, 500, 600, 700, 800, 900 are illustrated for the purpose of describing the removal of the flow conducting device 360, without introducing contaminations or microorganisms into the reservoir. The flow conducting device can be an infusion set or an injection needle, depending on the type of drug delivery device and treatment regimen to be applied.

Figure 3A:
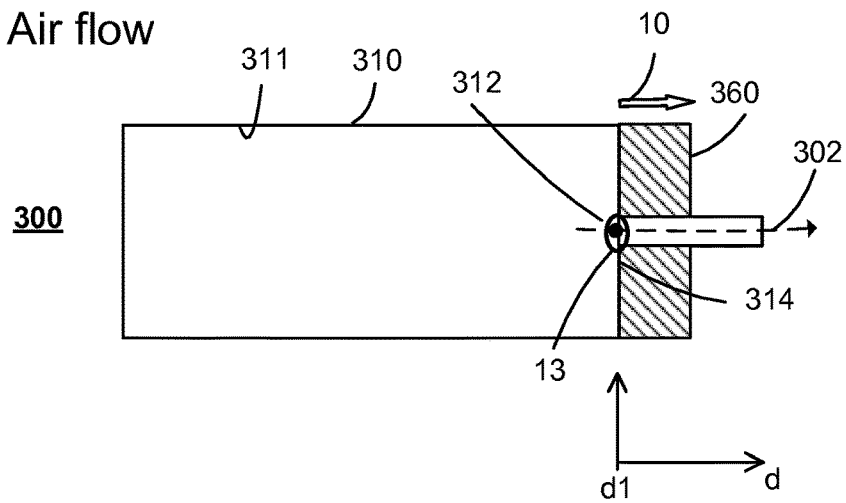
FIGS. 3A-3C illustrate schematically a drug delivery device according to the present disclosure during removal of a flow conducting device from a main portion of the drug delivery device, wherein contamination is prevented. The embodiment schematically illustrates a drug delivery device with a radially extending pressure seal.
Figure 3B:
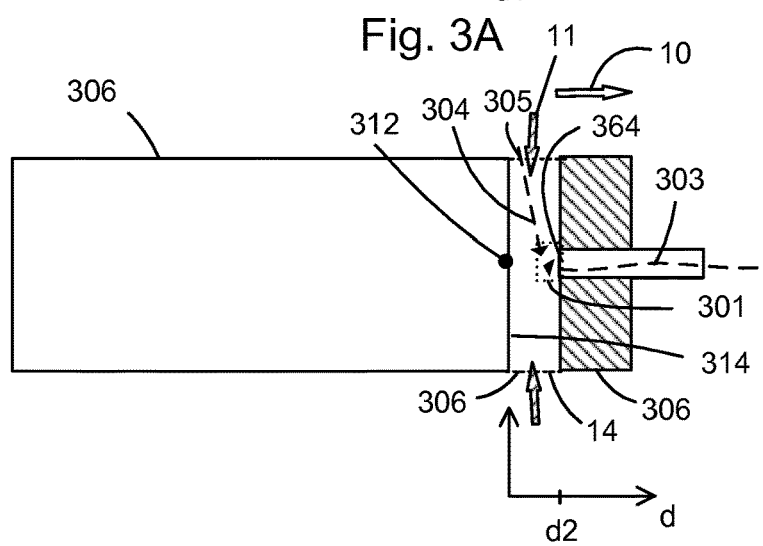
Figure 3C:
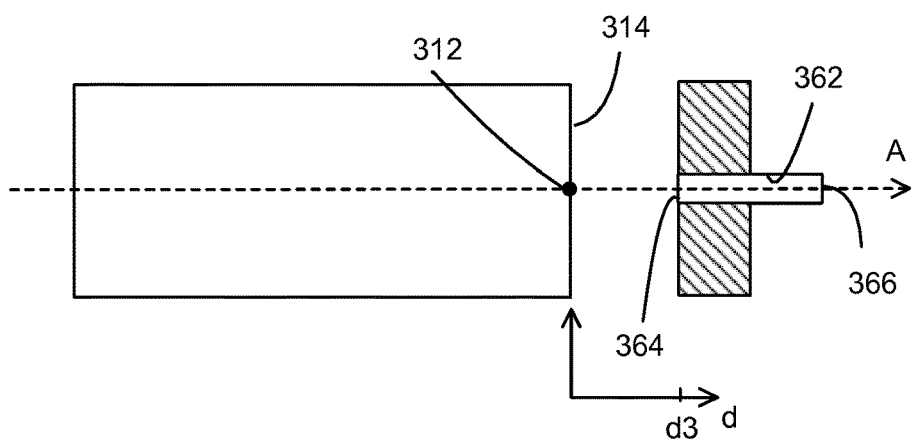

FIG. 3A-3C illustrate an embodiment of a multi-use drug delivery device 300 for extended use, wherein the drug delivery device is adapted for forming a radially extending pressure seal. The multi-use drug delivery device comprises a multi-use main portion 310 comprising a central axis (A) defining a longitudinal direction, and a single-use flow conducting device 360 which is to be exchanged during each drug delivery event. The flow conducting device is adapted for conducting drug to the subcutaneous tissue of a subject.

The drug delivery device is adapted to enable the flow conducting device to be movably arranged relative to the main portion, and the relative movement can be guided by cooperating structures of the main portion and the flow conducting device. The drug delivery device can be configured in a connected, an intermediate and an unconnected configuration.

In the connected configuration, which is illustrated in FIG. 3A, the flow conducting device 360 is arranged in a connected position relative to the main portion 310. The relative movement is guided, and the relative position, in this connected configuration, defines a first distance (d1) in the longitudinal direction between the flow conducting device and the main portion. The distance d1 is indicated on a coordinate system with a longitudinal axis originating in a fixed point in an outlet surface 314 of the main portion 310. In the connected configuration the distance d1 can be set to zero. The relative position, indicated by d1, corresponds to a first internal volume confined by an outer surface 306 of the drug delivery device 300. The solid ring 13 illustrate the area of wherein a pressure seal can be established, and the arrow 302 illustrate a combined flow path 302.

FIG. 3B illustrate the drug delivery device in the intermediate configuration, wherein the flow conducting device 360 is movably arranged in an intermediate position relative to the main portion 310. The relative movement is guided, and the relative position defines a second distance (d2) in the longitudinal direction between the flow conducting device and the main portion, which is larger than the first distance (d1). The relative position corresponds to a second internal volume confined by the outer surface 306 of the drug delivery device (300). The half dot rectangle indicates the area of a fluid communication volume.

FIG. 3C illustrate the unconnected configuration, wherein the flow conducting device 360 is arranged in an unconnected position relative to the main portion 310. The relative movement is not guided, and the main portion and the flow conducting device are not connected.

In order to change between configurations, the drug delivery device is adapted to change configuration by moving the flow conducting device in the longitudinal direction and relative to the main portion 310. The change from the connected configuration to the unconnected configuration is obtained through the intermediate configuration.

As the second internal volume is larger than the first internal volume, the internal volume confined by the outer surface 306 of the drug delivery device expands, in response to changing the drug delivery device from the connected configuration to the intermediate configuration. If the confined volume is isolated from the surroundings, an expansion of a confined volume will inevitably be associated with a corresponding pressure drop.

The main portion 310 of the drug delivery device comprises a pressurizable drug reservoir 311, e.g. pressurizable by moving a piston, a drug expelling mechanism, for pressurizing the reservoir and thereby expelling an amount of drug. The reservoir comprises multiple doses of a liquid drug formulation, and the drug formulation allows microbial growth upon introduction of microorganisms into the reservoir during extended use. Therefore, introduction of microorganisms should be avoided during use. The main portion 310 further comprises a drug outlet 312 and an outlet surface 314, wherein the outlet surface provides a portion of an outer surface of the main portion. The flow conducting device 360 comprises a flow channel 362 comprising a channel inlet 364 and a channel outlet 366. The flow channel is adapted for forming the combined flow path 302, with the drug outlet 312. The flow conducting device 360 further comprises an inlet surface 368 for interfacing the outlet surface 314 of the main portion.

The drug delivery device further comprises and defines a fluid communication volume 301 being a fluid or gaseous volume at the channel inlet 364. The drug delivery device also defines an unintended flow path 303 extending from the channel outlet 366 through the flow channel 362 and to the fluid communication volume 301.

The connected configuration, FIG. 3A further comprises and is further defined by the outlet surface 314 interfacing the inlet surface 368. The drug outlet 312 is arranged in the outlet surface 314 to allow the drug to flow from the main portion to the flow conducting device along the combined flow path 302, in response to the pressure in the reservoir exceeds a pressure threshold during the administration of a dose. The fluid communication volume provides a portion of the combined flow path and the first internal volume of the drug delivery device 300.

The unconnected configuration, FIG. 3C, further comprises and is further defined by the outlet surface interfacing or being directly exposed to the external environment, the drug outlet 312 is arranged in a closed state, and the drug outlet is arranged to inhibit the introduction of microorganisms from the external environment and into the reservoir. As discussed later, in some embodiments effect can be provided by providing a check valve at the outlet. In alternative embodiments the effect is provided by ensuring that the outlet is only arranged in the outlet surface in the connected configuration, i.e., a sliding valve member can change the appearance of the outlet surface. In one position the valve member can hide the outlet an in another position it provides the outlet in the outlet surface. In alternative embodiments a sliding valve covering and uncovering the outlet in the unconnected and connected state, respectively, can be combined with a check valve in the outlet or between the outlet and the reservoir.

The intermediate configuration further comprises an equalizing channel defining an equalizing flow path 304, which is different from the unintended flow path. The equalizing flow path 304 is adapted for equalizing the fluid pressure in the fluid communication volume 301 to the fluid pressure at the channel outlet 366, upon changing the configuration from the connected to the intermediate configuration. As explained, by change of configuration the internal volume confined by the outer surface 306 is expanding the internal volume. The equalizing channel is adapted to ensure that, in response to the expansion, an equalizing fluid flow along the equalizing flow path is larger than an unintended flow along the unintended flow path. Hereby, equalization of the fluid communication volume is provided with a reduced risk of introducing microorganisms from the flow channel 362 into the reservoir 311. Ideally, the equalizing channel is adapted to eliminate a fluid flow along the unintended flow path 303. In this embodiment, wherein the pressure seal is formed in the radial direction, the equalizing channel along the pressure seal expands proportionally to the relative movement of the main portion and the flow conducting device, which provides an equalizing channel with a low flow resistance.

The outlet 312 can in some alternative embodiments be provided in the outlet surface 314. If the outlet 312 is provided in the outlet surface 314, no portions of the flow conducting device will be allowed to enter an internal volume of the main portion 310, as the internal volume of the main portion is partly confined by the outlet surface interfacing the flow conducting device 360.

Figure 4A:
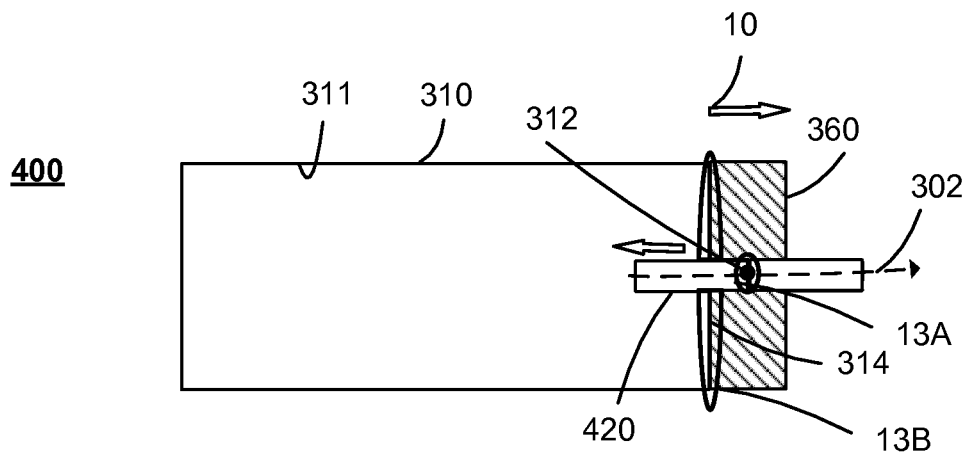
FIGS. 4A-4C illustrate schematically a drug delivery device according to the present disclosure during removal of a flow conducting device from a main portion of the drug delivery device, wherein contamination is prevented. The embodiment schematically illustrates a drug delivery device with a radially extending pressure seal, and an outlet retracting during the removal.
Figure 4B:
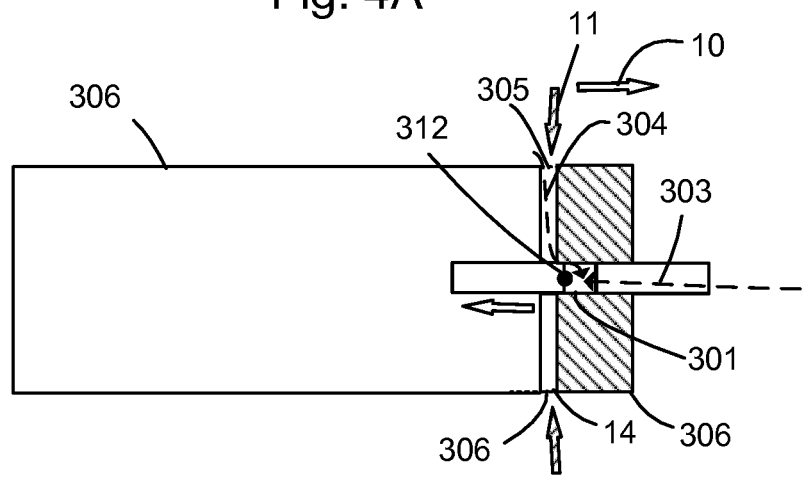
Figure 4C:
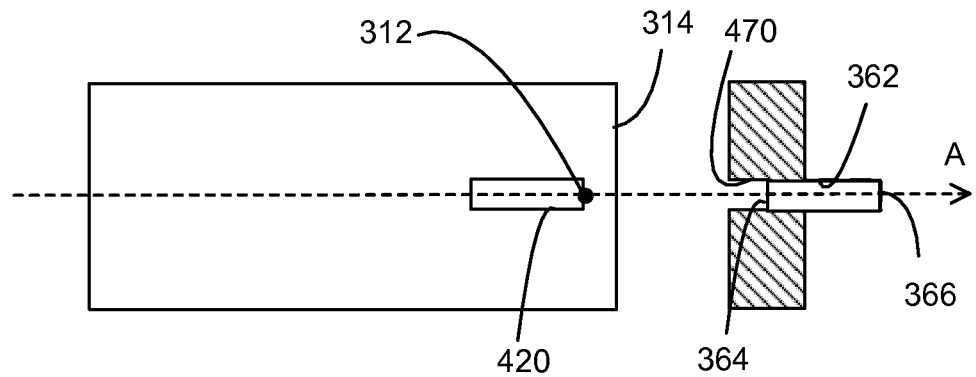

FIG. 4A-4C illustrate an embodiment of a multi-use drug delivery device 400 for extended use, wherein the drug delivery device is also adapted for forming a radially extending pressure seal. In this alternative variation of the embodiment illustrated in FIG. 3, the main portion 310 comprises a extendable piercing needle, which penetrates the outlet surface 314 in the embodiment of a pierceable septum. In the connected configuration illustrated in FIG. 4A, the extendable needle pierces the septum, and establishes a combined flow path with the flow conducting device. The outlet 312 is provided in the outlet surface in the connected configuration. The pressure seal can be established in the area indicated by solid ring 13A or alternatively 13B. In the intermediate configuration illustrated in FIG. 4B the extendable needle 420 is retracting from a receiving portion 470, as the main portion 310 and the flow conducting device are separated by the relative guided movement, and the internal volume of the drug delivery device, confined by outer surface 306, expands. In the unconnected configuration illustrated in FIG. 3C, the extendable piercing needle has been retracted into a proximal position, wherein the outlet is protected and enclosed by the septum.

The intermediate configuration further comprises an equalizing channel defining an equalizing flow path 304, which is different from the unintended flow path. The equalizing flow path 304 is adapted for equalizing the fluid pressure in the fluid communication volume 301 to the fluid pressure at the channel outlet 366, upon changing the configuration from the connected to the intermediate configuration. As explained, by change of configuration the internal volume confined by the outer surface 306 is expanding the internal volume. The equalizing channel is adapted to ensure that, in response to the expansion, an equalizing fluid flow along the equalizing flow path is larger than an unintended flow along the unintended flow path. Hereby, equalization of the fluid communication volume is provided with a reduced risk of introducing microorganisms from the flow channel 362 into the reservoir 311. Ideally, the equalizing channel is adapted to eliminate a fluid flow along the unintended flow path 303.

Figure 5A:
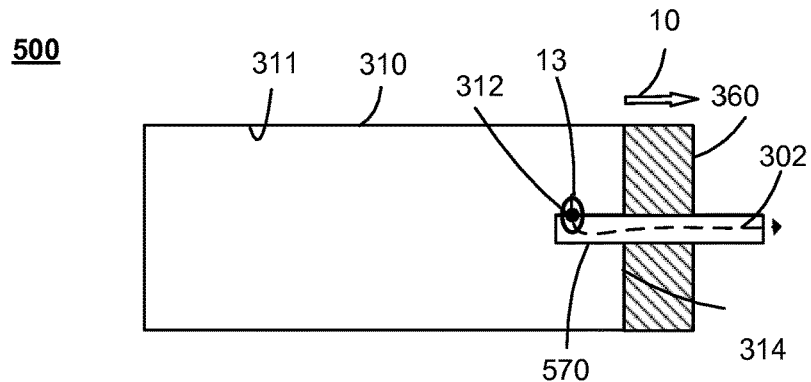
FIGS. 5A-5C illustrate schematically of a drug delivery device according to the present disclosure during removal of a flow conducting device from a main portion of the drug delivery device, wherein contamination is prevented. The embodiment schematically illustrates a drug delivery device with a longitudinally extending pressure seal, wherein a fluid communication volume is confined and sealed until the intermediate configuration.
Figure 5B:
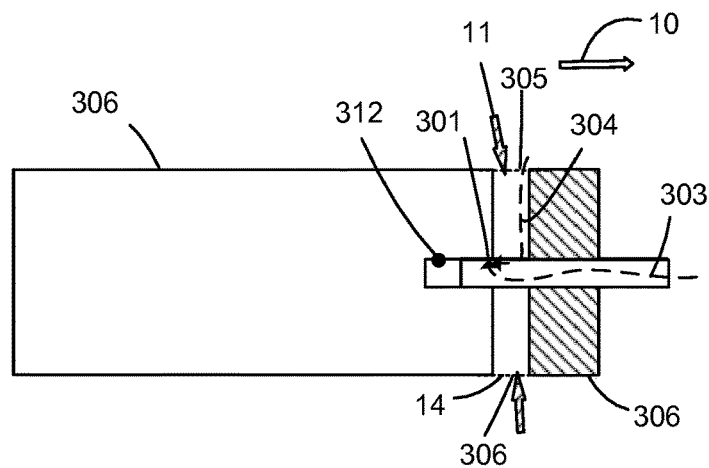
Figure 5C:
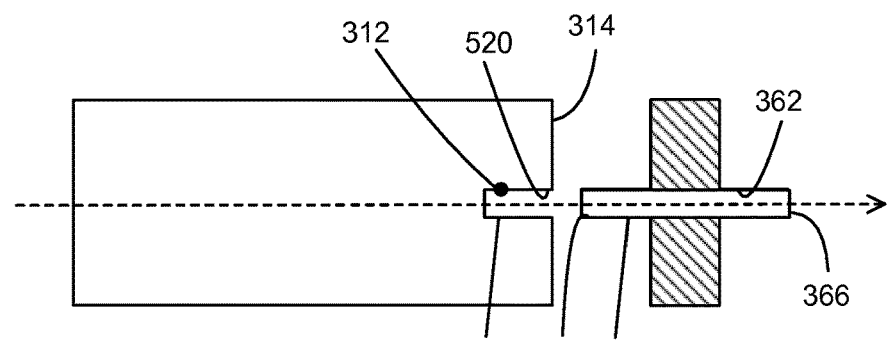

FIG. 5A-5C illustrate an embodiment of a multi-use drug delivery device 300 for extended use, wherein the drug delivery device is adapted for forming a longitudinally extending pressure seal. The multi-use drug delivery device comprises a multi-use main portion 310 comprising a central axis (A) defining a longitudinal direction, and a single-use flow conducting device 360 which is to be exchanged during each drug delivery event. The flow conducting device is adapted for conducting drug to the subcutaneous tissue of a subject.

The drug delivery device is adapted to enable the flow conducting device to be movably arranged relative to the main portion, and the relative movement can be guided by cooperating structures of the main portion and the flow conducting device. The drug delivery device can be configured in a connected, an intermediate and an unconnected configuration.

The main portion 310 comprises a receiving portion 520, and the flow conducting device 360 comprises a proximal portion 570, wherein the receiving portion 520 is adapted for receiving proximal portion in the connected state.

In the connected configuration, which is illustrated in FIG. 5A, the flow conducting device 360 is arranged in a connected position relative to the main portion 310. The relative movement is guided, and the relative position, in this connected configuration, defines a first distance (d1 not shown on FIG. 5 but could be illustrated in analogy with FIG. 3) in the longitudinal direction between the flow conducting device and the main portion. In the connected configuration the distance d1 can be set to zero. The relative position, indicated by d1, corresponds to a first internal volume confined by an outer surface 306 of the drug delivery device 300. The solid ring 13 illustrate the area of wherein a pressure seal can be established, and the arrow 302 illustrate a combined flow path 302.

FIG. 5B illustrate the drug delivery device in the intermediate configuration, wherein the flow conducting device 360 is movably arranged in an intermediate position relative to the main portion 310. The relative movement is guided, and the relative position defines a second distance (d2) in the longitudinal direction between the flow conducting device and the main portion, which is larger than the first distance (d1). The relative position corresponds to a second internal volume confined by the outer surface 306 of the drug delivery device (300). The half dot rectangle indicates the area of a fluid communication volume.

FIG. 5C illustrate the unconnected configuration, wherein the flow conducting device 360 is arranged in an unconnected position relative to the main portion 310. The relative movement is not guided, and the main portion and the flow conducting device are not connected.

In order to change between configurations, the drug delivery device is adapted to change configuration by moving the flow conducting device in the longitudinal direction and relative to the main portion 310. The change from the connected configuration to the unconnected configuration is obtained through the intermediate configuration.

As the second internal volume is larger than the first internal volume, the internal volume confined by the outer surface 306 of the drug delivery device expands, in response to changing the drug delivery device from the connected configuration to the intermediate configuration. If the confined volume is isolated from the surroundings, an expansion of a confined volume will inevitably be associated with a corresponding pressure drop.

The main portion 310 of the drug delivery device comprises a pressurizable drug reservoir 311, e.g. pressurizable by moving a piston, a drug expelling mechanism, for pressurizing the reservoir and thereby expelling an amount of drug. The reservoir comprises multiple doses of a liquid drug formulation, and the drug formulation allows microbial growth upon introduction of microorganisms into the reservoir during extended use. Therefore, introduction of microorganisms should be avoided during use. The main portion 310 further comprises a drug outlet 312 and an outlet surface 314, wherein the outlet surface provides a portion of an outer surface of the main portion. The flow conducting device 360 comprises a flow channel 362 comprising a channel inlet 364 and a channel outlet 366. The flow channel is adapted for forming the combined flow path 302, with the drug outlet 312. The flow conducting device 360 further comprises an inlet surface 368 for interfacing the outlet surface 314 of the main portion.

The drug delivery device further comprises and defines a fluid communication volume 301 being a fluid or gaseous volume at the channel inlet 364, and confined between the inlet 364 and the outlet surface 314. The drug delivery device also defines an unintended flow path 303 extending from the channel outlet 366 through the flow channel 362 and to the fluid communication volume 301.

The connected configuration, FIG. 5A further comprises and is further defined by the outlet surface 314 interfacing the inlet surface 368. The drug outlet 312 is arranged in the outlet surface 314 to allow the drug to flow from the main portion to the flow conducting device along the combined flow path 302, in response to the pressure in the reservoir exceeds a pressure threshold during the administration of a dose. The fluid communication volume provides a portion of the combined flow path and the first internal volume of the drug delivery device 300. The outlet 312 is provided in the outlet surface 314.

The unconnected configuration, FIG. 5C, further comprises and is further defined by the outlet surface 314 interfacing or being directly exposed to the external environment, the drug outlet 312 is arranged in a closed state, and the drug outlet is arranged to inhibit the introduction of microorganisms from the external environment and into the reservoir.

The intermediate configuration further comprises an equalizing channel defining an equalizing flow path 304, which is different from the unintended flow path. The equalizing flow path 304 is adapted for equalizing the fluid pressure in the fluid communication volume 301 to the fluid pressure at the channel outlet 366, upon changing the configuration from the connected to the intermediate configuration. As explained, by change of configuration the internal volume confined by the outer surface 306 is expanding the internal volume. The equalizing channel is adapted to ensure that, in response to the expansion, an equalizing fluid flow along the equalizing flow path is larger than an unintended flow along the unintended flow path. Hereby, equalization of the fluid communication volume is provided with a reduced risk of introducing microorganisms from the flow channel 362 into the reservoir 311. Ideally, the equalizing channel is adapted to eliminate a fluid flow along the unintended flow path 303. In this embodiment, wherein the pressure seal is formed in the longitudinal direction, the equalizing channel along the pressure seal expands or changes flow resistance with radial variations in the interface between the outlet surface 314 and the inlet surface 368. When the drug delivery device changes from the connected configuration to the intermediate configuration illustrated in FIG. 5B there is large variation in the interface, which provides an equalizing channel with a low flow resistance. In alternative embodiments, channels are further provided to equalize the volume of fluid in communication with the drug outlet. Alternatively, a check valve with a sufficient threshold ensures that liquid is not withdrawn from the outlet upon removal of the flow conducting device.

In the illustrated embodiment of FIG. 5, the outlet 312 is provided in the outlet surface 314. When the outlet 312 is provided in the outlet surface 314, no portions of the flow conducting device will be allowed to enter an internal volume of the main portion 310, as the internal volume of the main portion is partly confined by the outlet surface interfacing the flow conducting device 360.

Figure 6A:
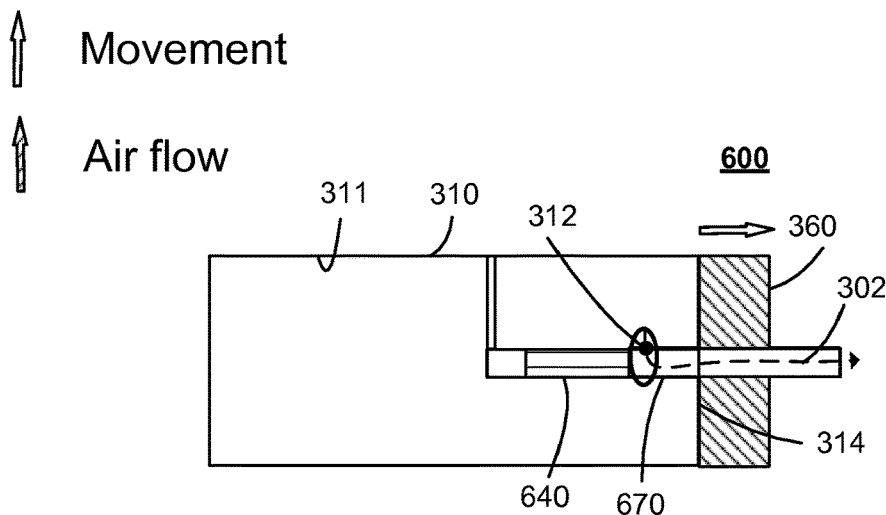
FIGS. 6A-6C illustrate schematically a drug delivery device according to the present disclosure during removal of a flow conducting device from a main portion of the drug delivery device, wherein contamination is prevented. The embodiment schematically illustrates a drug delivery device with a longitudinally extending pressure seal, and a movable valve member, wherein a fluid communication volume is confined and sealed until the intermediate configuration.
Figure 6B:
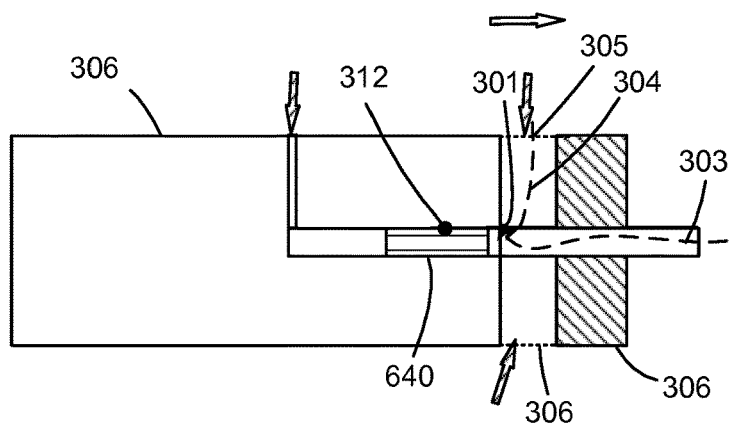
Figure 6C:
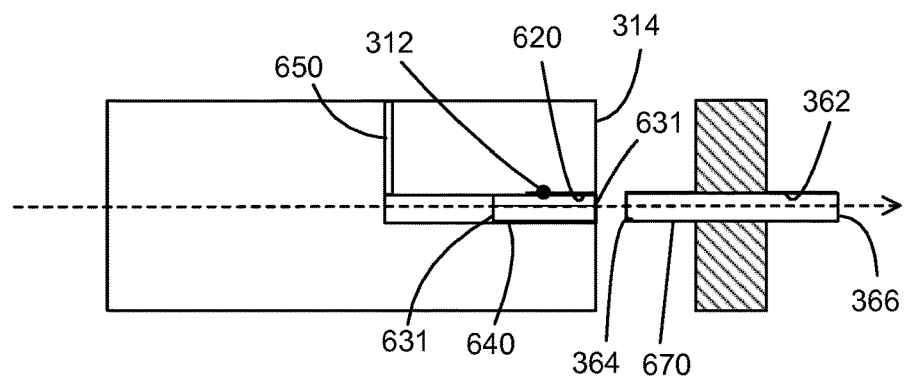

FIG. 6A-6C illustrate an embodiment of a multi-use drug delivery device 300 for extended use, wherein the drug delivery device is adapted for forming a longitudinally extending pressure seal, as for the embodiment illustrated in FIG. 5. In addition to the embodiment of FIG. 5, the embodiment of FIG. 6 comprises a movable valve 640 adapted to expose the outlet 312 in the connected configuration. The main portion further comprises a support structure 620 to support the movable valve, and the flow conducting device comprises a proximal portion 670 to manipulate the position of the movable valve 640.

The drug delivery device is adapted to enable the flow conducting device to be movably arranged relative to the main portion, and the relative movement can be guided by cooperating structures of the main portion and the flow conducting device. The drug delivery device can be configured in a connected (FIG. 6A), an intermediate (FIG. 6B) and an unconnected configuration (FIG. 6C). In some embodiments, a channel 650 ensures that the pressure due to movement of the valve can be equalized.

Figure 7A:
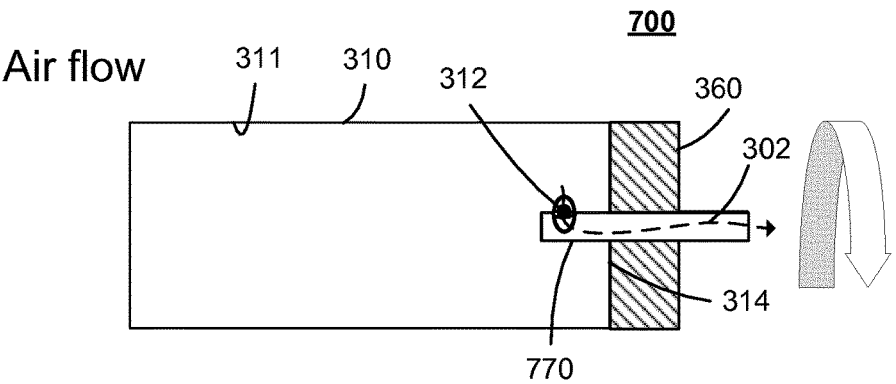
FIGS. 7A-7D illustrate schematically a drug delivery device according to the present disclosure during removal of a flow conducting device from a main portion of the drug delivery device, wherein contamination is prevented. The embodiment schematically illustrates a drug delivery device with a longitudinally extending pressure seal, and a movable valve member, wherein a fluid communication volume is confined and sealed until the intermediate configuration. The flow conducting device is turned during removal.
Figure 7B:
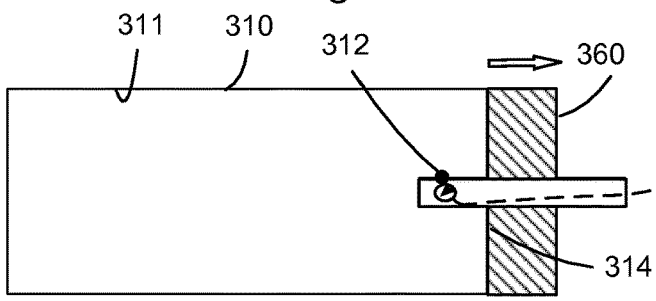
Figure 7C:
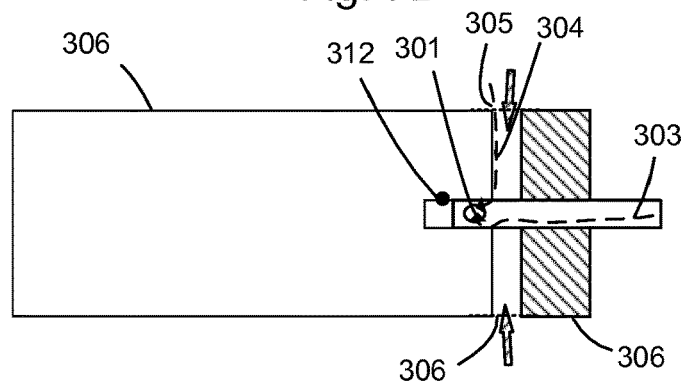

FIG. 7A-7D illustrate an embodiment of a multi-use drug delivery device 300 for extended use, wherein the drug delivery device is adapted for forming a longitudinally extending pressure seal, as for the embodiment illustrated in FIG. 5. In addition to the embodiment of FIG. 5, the embodiment of FIG. 7 comprises a turnable flow conducting member 360 adapted to break the pressure seal form in the connected configuration by turning the flow conducting device relative to the main portion 310. The turned configuration is illustrated in FIG. 7B.

Figure 7D:
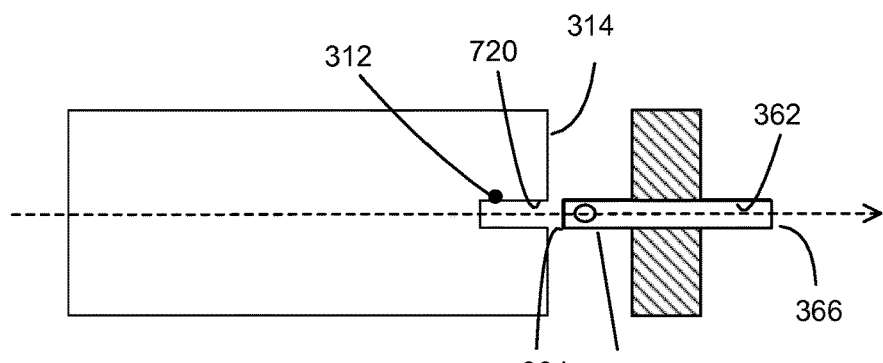
Figure 8A:
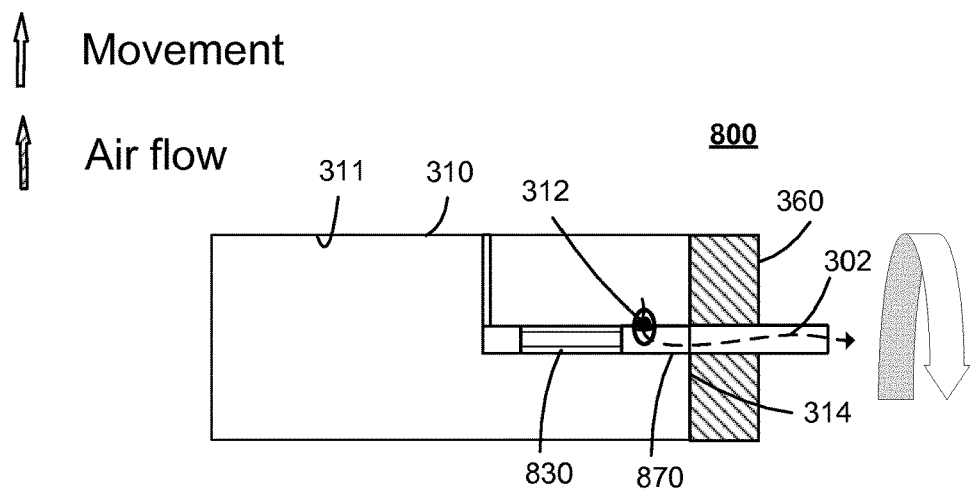
FIGS. 8A-8D illustrate schematically a drug delivery device according to the present disclosure during removal of a flow conducting device from a main portion of the drug delivery device, wherein contamination is prevented. The embodiment schematically illustrates a drug delivery device with a longitudinally extending pressure seal, and a movable valve member, wherein a fluid communication volume is confined and sealed until the intermediate configuration. The flow conducting device is turned during removal and an air inlet ensures equalization during movement of the valve member.
Figure 8B:
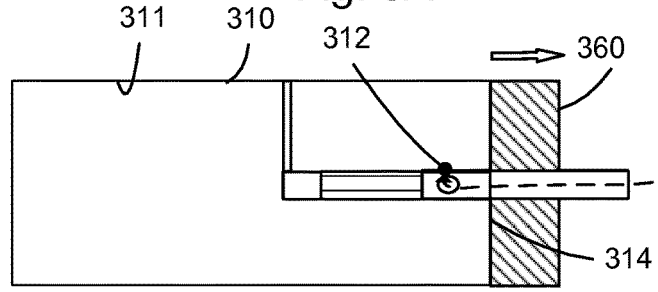
Figure 8C:
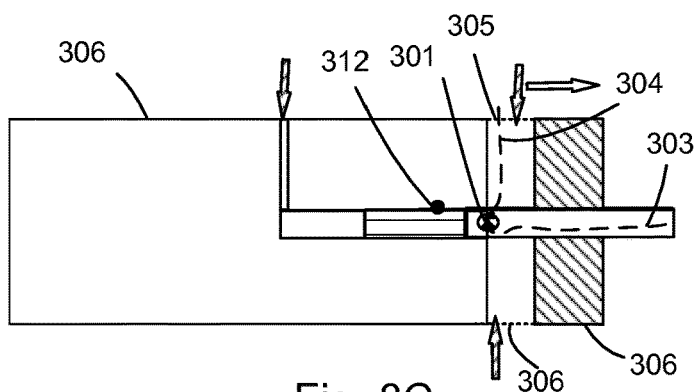
Figure 8D:
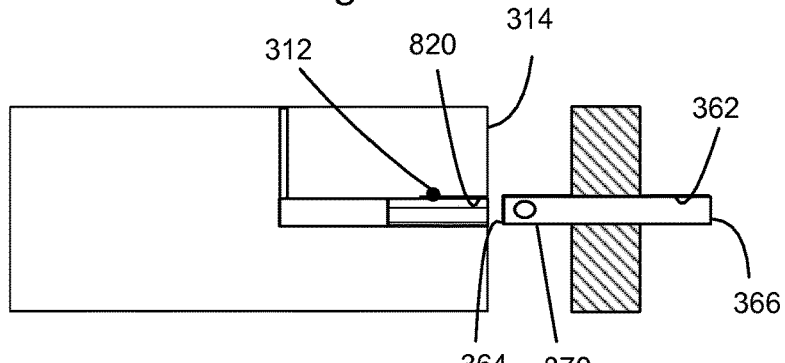
Figure 9A:
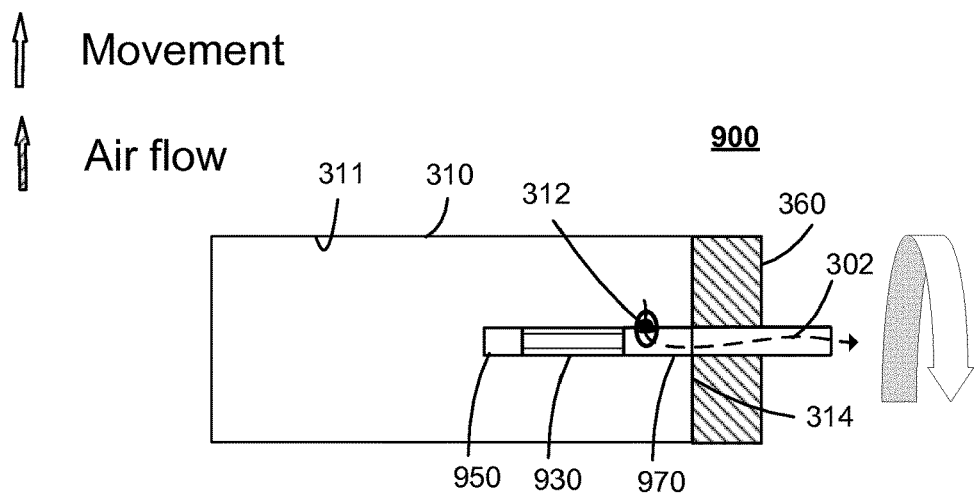
FIGS. 9A-9D illustrate schematically a drug delivery device according to the present disclosure during removal of a flow conducting device from a main portion of the drug delivery device, wherein contamination is prevented. The embodiment schematically illustrates a drug delivery device with a longitudinally extending pressure seal, and a movable valve member, wherein a fluid communication volume is confined and sealed until the intermediate configuration. The flow conducting device is turned during removal and an internal chamber is pressurized during movement of the valve member.
Figure 9B:
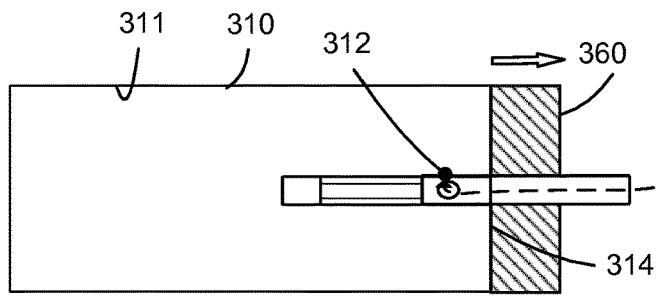
Figure 9C:
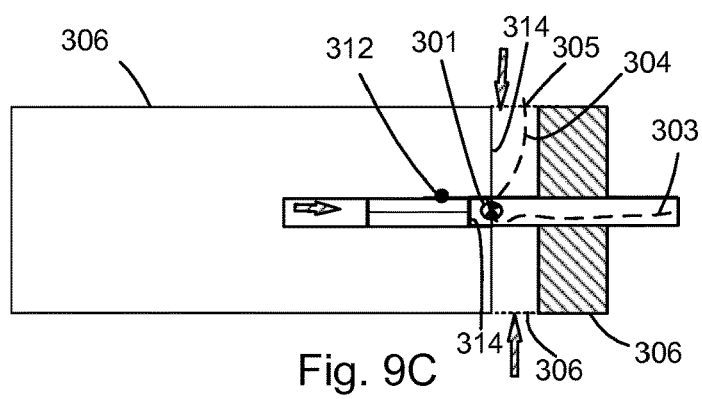
Figure 9D:
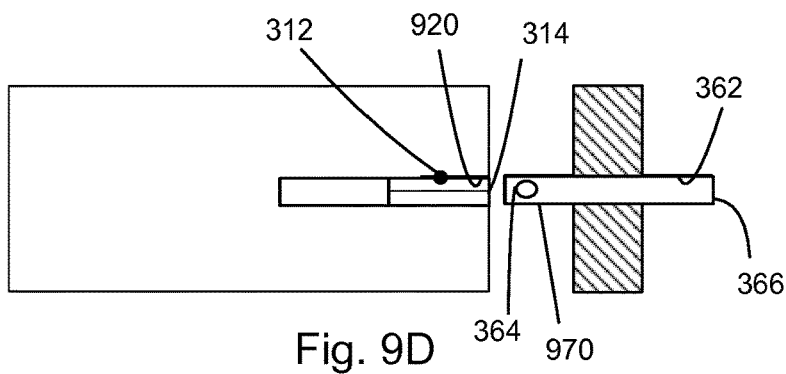

The drug delivery device is adapted to enable the flow conducting device to be movably arranged relative to the main portion, and the relative movement can be guided by cooperating structures of the main portion and the flow conducting device. The drug delivery device can be configured in a connected (FIG. 7A), an intermediate (FIG. 7C) and an unconnected configuration (FIG. 7D). In some embodiments, a channel 650 ensures that the pressure due to movement of the valve can be equalized.

In this embodiment, wherein the pressure seal is formed in the longitudinal direction, the equalizing channel along the pressure seal expands or changes flow resistance with radial variations in the interface between the outlet surface 314 and the inlet surface 368. When the drug delivery device changes from the connected configuration to the turned configuration illustrated in FIG. 7B there can be variations in the interface, which provides an equalizing channel when the flow conducting device is removed and thereby momentarily enters the intermediate configuration.

FIG. 8 illustrates an embodiment of the present disclosure, which in addition to the embodiment illustrated in FIG. 7 comprises a movable valve, a valve supporting structure 820, and a proximal portion 870 of the flow conducting device 360. FIG. 8A illustrates the connected configuration, FIG. 8B illustrate the turned configuration, FIG. 8C illustrate the intermediate configuration, and FIG. 8D illustrate the unconnected configuration.

FIG. 9 illustrates an embodiment of the present disclosure, which in addition to the embodiment illustrated in FIG. 8 comprises a pressure chamber 950, wherein the pressure changes upon movement of the movable valve 930. In a retracted position of the valve 930, the pressure in the chamber 950 is increased and urges the valve member in towards an extended position, wherein the distal surface of the valve member 950 is flush with the remaining outlet surface 314. FIG. 9A illustrates the connected configuration, FIG. 9B illustrate the turned configuration, FIG. 9C illustrate the intermediate configuration, and FIG. 9D illustrate the unconnected configuration.

Figure 10A:
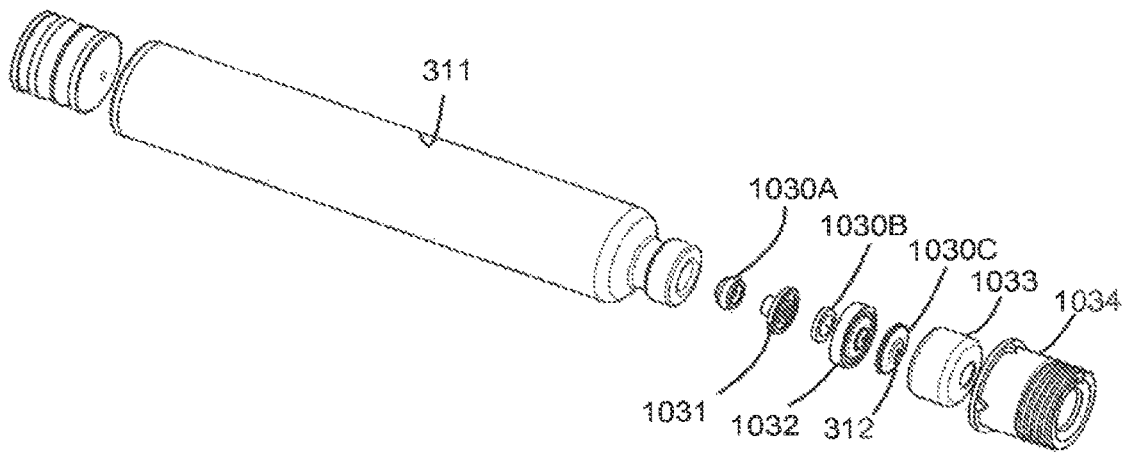
FIGS. 10A-10C illustrate an embodiment according to the present disclosure, the embodiment provides a radially extending pressure seal in the connected configuration illustrated in FIG. 10B. The unconnected configuration is illustrated in FIG. 10C but without the flow conducting device.
Figure 10B:
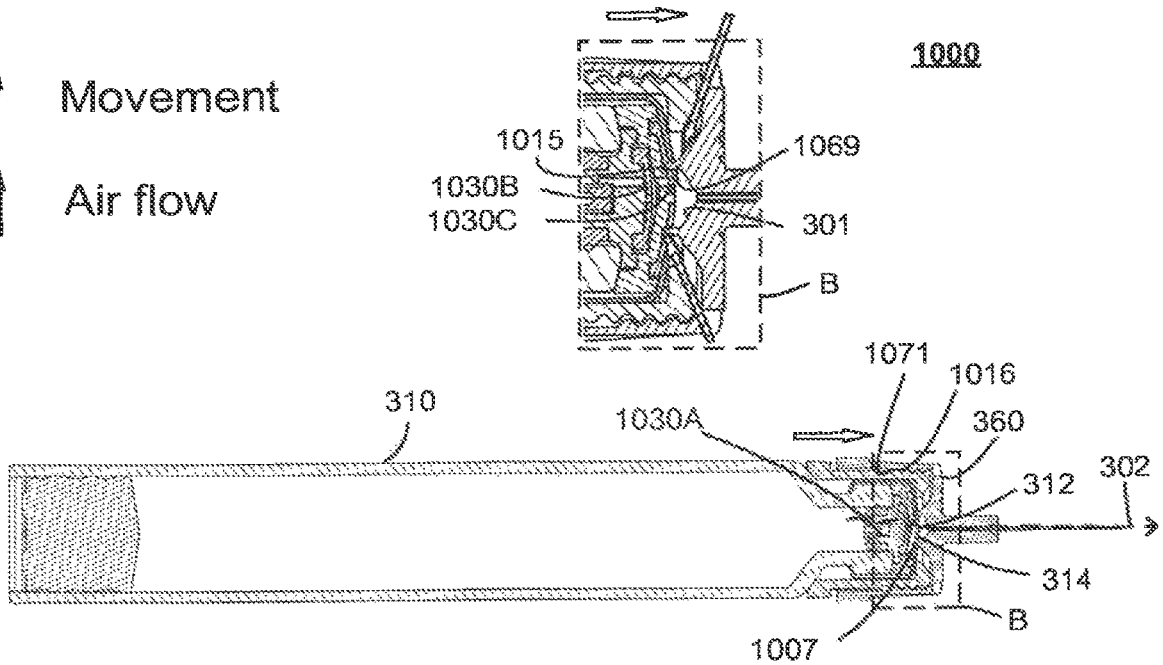
Figure 10C:
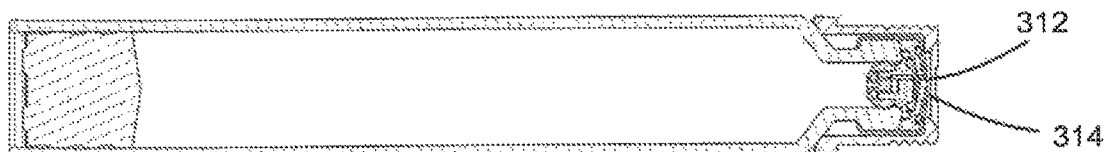

FIG. 10 illustrates an embodiment of a multi-use drug delivery device 1000 according to the present disclosure comprising a proximal check valve 1030A interfacing the drug reservoir, a proximal support member 1031 supporting the proximal check valve 1030A an provides a valve seat. The proximal supporting member 1031 is further adapted for supporting and providing a valve seat for an intermediate check valve 1030B. The drug delivery device further comprises a distal support member 1032 providing support and a valve seat for a distal check valve 1030C. The check valves and support members are formed as disk like shapes and are stacked together in a flow communication unit. The flow communication unit can be secured to the reservoir by a cap 1033, and a code top 1034 provides a connection to the flow conducting device 360. FIG. 10B illustrates the drug delivery device in the connected configuration and an enlarged area B. FIG. 10C illustrates the main portion in the unconnected configuration. When the drug delivery device is changed from the connected to the unconnected it will enter an intermediate configuration, in analogy to the illustrated embodiment in FIG. 3.

Figure 11A:
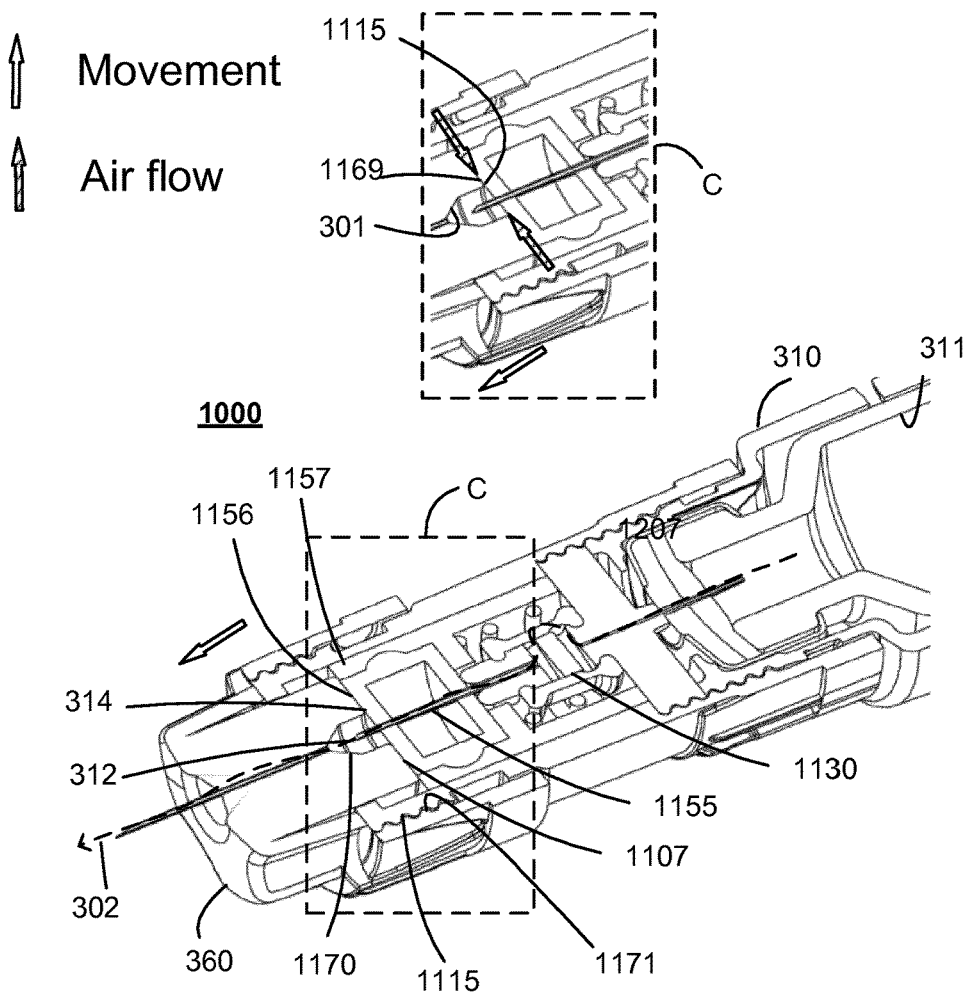
FIGS. 11A-11B illustrate an embodiment according to the present disclosure, the embodiment provides a radially extending pressure seal in the connected configuration illustrated in FIG. 11A. The unconnected configuration is illustrated in FIG. 11B.
Figure 11B:
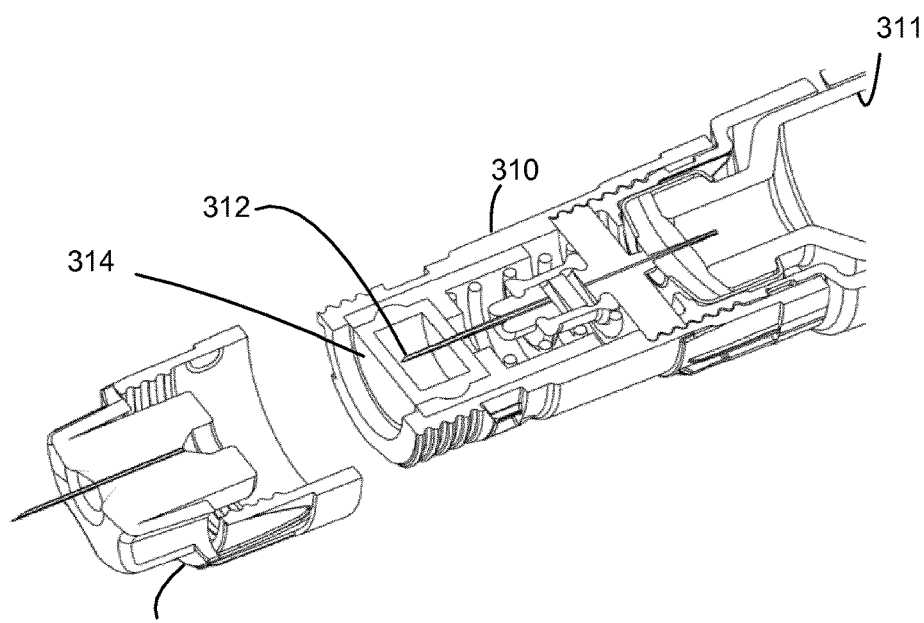

FIG. 11 illustrates an embodiment of a multi-use drug delivery device 1100 according to the present disclosure comprising an intermediate check valve 1130 position between an inlet and an outlet of an internal channel. A distal portion of the internal flow channel is provided by a distal piercing needle 1155 adapted to pierce a septum 1156. The main portion comprises a distal movable portion 1157 with the septum 1156 provided on a distal end. The flow conducting device, illustrated as a pen needle, comprises a receiving portion 1170 adapted to receive the distal piercing needle 1155 and provide a portion of the combined flow path 302. The distal movable portion 1157 is adapted to be pushed to a proximal position by the flow conducting device, when the drug delivery device is in the connected configuration illustrated in FIG. 11A, wherein the combined flow path 302 is provided, as the piercing needle 1155 pierces the septum 1156 and is received in the receiving portion 1170. The distal movable portion 1157 is further adapted to be urged to a distal position, when the drug delivery device is in the unconnected configuration illustrated in FIG. 11B. In the unconnected configuration the piercing needle 1155 is retracted to a position covered by the septum 1156, i.e., the needle does not pierce the septum. FIG. 11A illustrates the drug delivery device in the connected configuration and an area C illustrating further details. FIG. 11B illustrates the main portion in the unconnected configuration. When the drug delivery device is changed from the connected to the unconnected it will enter an intermediate configuration, in analogy to the illustrated embodiment in FIG. 4.

Figure 12A:
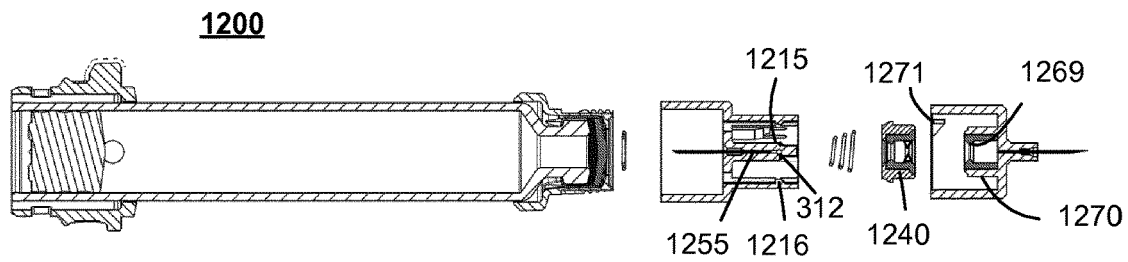
FIGS. 12A-12C illustrate an embodiment according to the present disclosure, the embodiment provides a longitudinally extending pressure seal in the connected configuration illustrated in FIG. 12B. The unconnected configuration is illustrated in FIG. 12C.
Figure 12B:
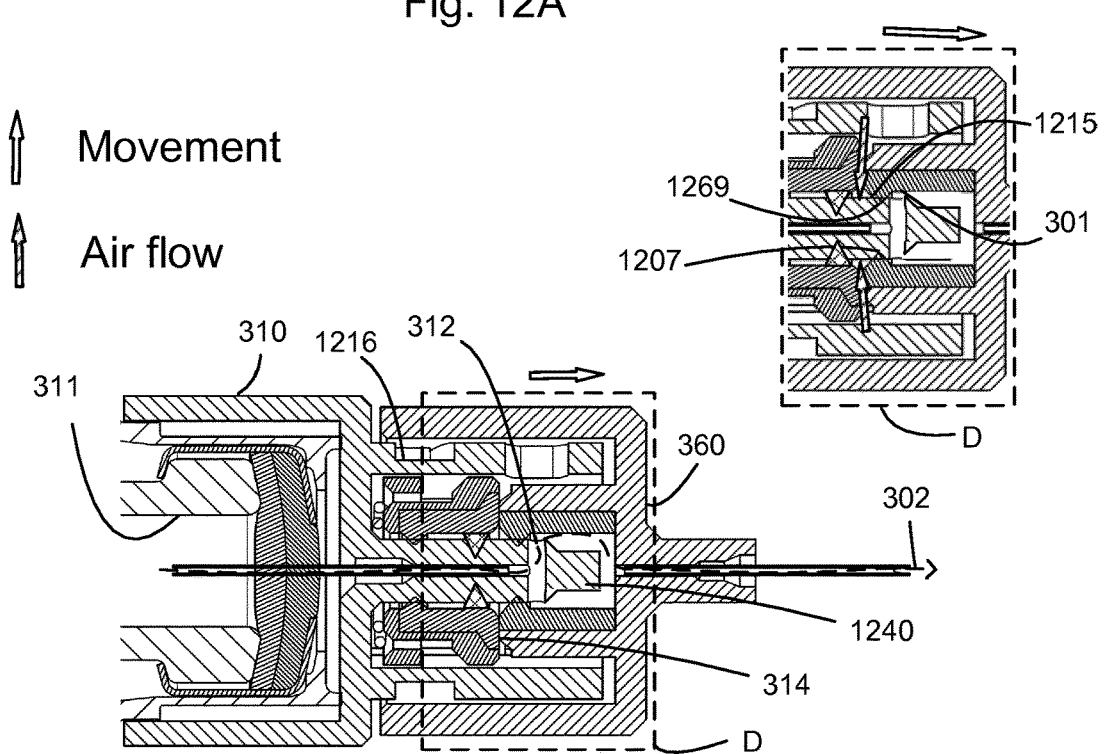
Figure 12C:
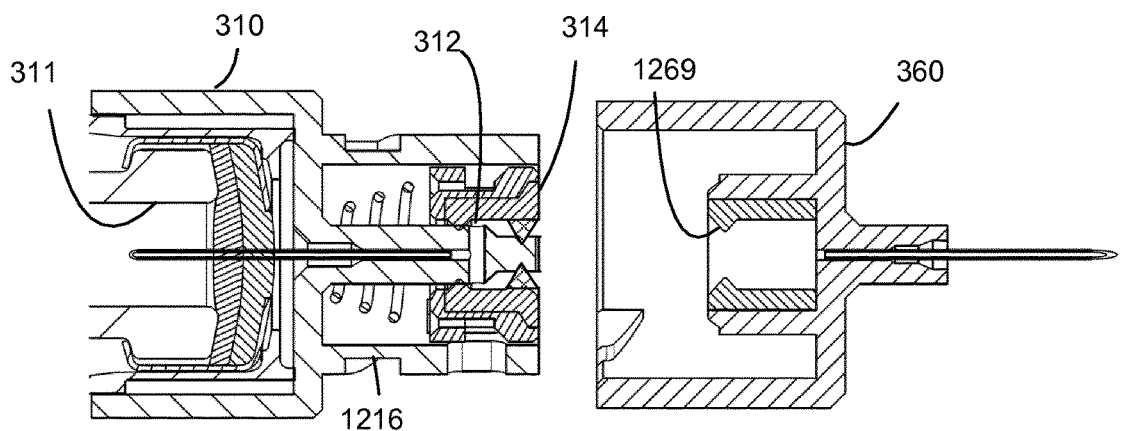

FIG. 12 illustrates an embodiment of a multi-use drug delivery device 1200 according to the present disclosure, wherein the main portion 310 comprises a central channel portion 1255 comprising a proximal piercing needle, a central support structure, and radial channel outlets 312 (one on each side). The proximal piercing needle is in fluid communication with the reservoir 311. The main portion 310 further comprises a movable valve member 1240, sliding on a radial surface of the central channel portion and adapted to be positioned in a normally closed distal position wherein the outlets 312 are closed and an open proximal position, wherein the outlets 312 are positioned in the outlet surface 314. The flow conducting device 360 comprises a receiving portion 1270 adapted to receive the central channel portion 1255 with the outlets 312, and thereby form the combined flow path 302. A check valve 1230 can be provided along the central channel. FIG. 12B illustrates the drug delivery device in the connected configuration and an enlarged area D. FIG. 12C illustrates the drug delivery device in the unconnected configuration. When the drug delivery device is changed from the connected to the unconnected it will enter an intermediate configuration, in analogy to the illustrated embodiments in FIGS. 5-9.

Figure 13A:
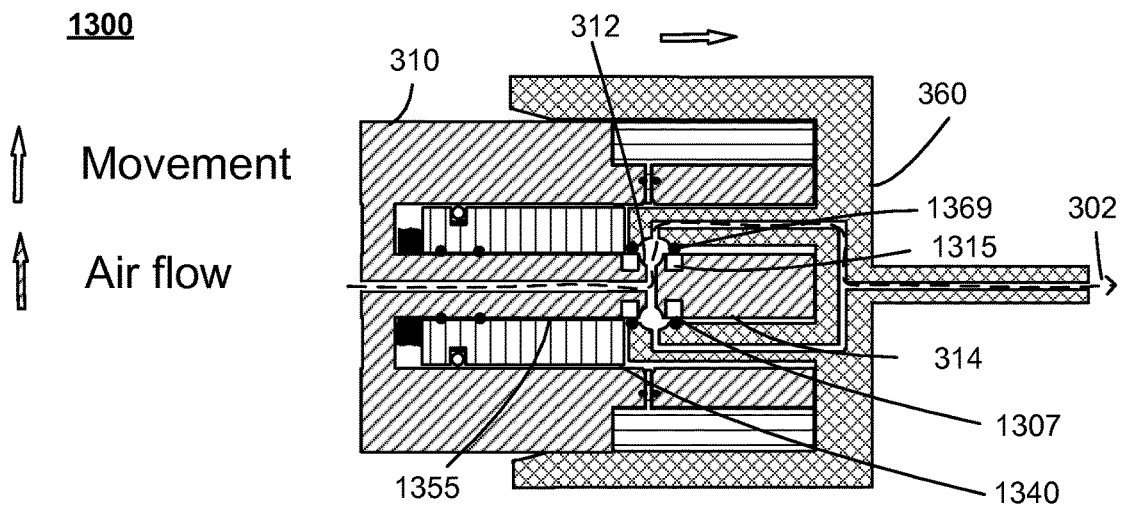
FIGS. 13A-13C illustrate an embodiment according to the present disclosure, the embodiment provides a longitudinally extending pressure seal in the connected configuration illustrated in FIG. 12B. The unconnected configuration is illustrated in FIG. 12C. The illustrated drug delivery device is adapted to provide confined and sealed fluid communication volume between the connected, FIG. 13A, and the intermediate configuration, FIG. 13B.
Figure 13B:
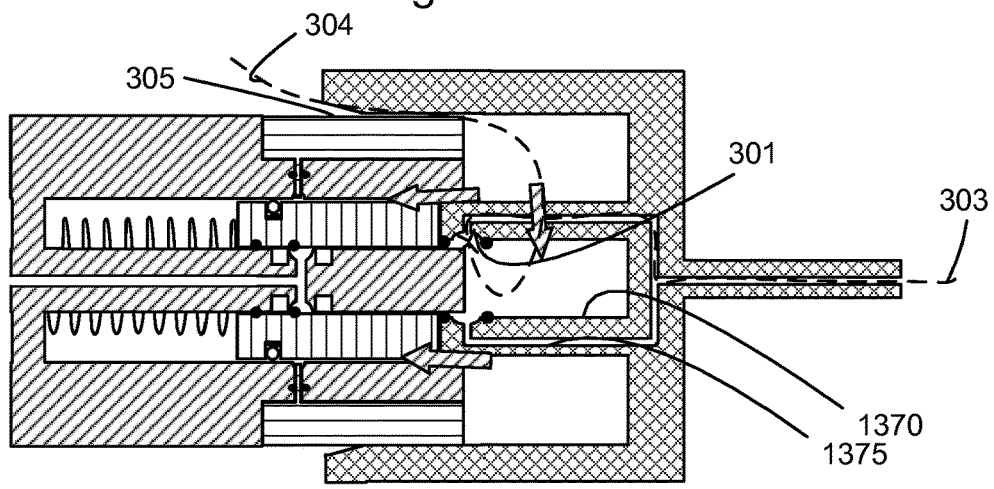
Figure 13C:
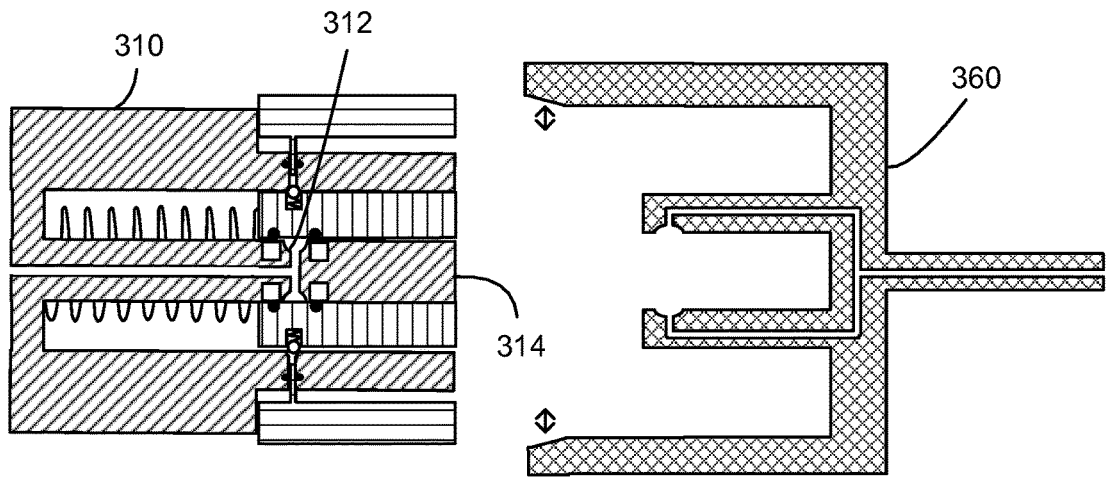

FIG. 13 illustrates an embodiment of a multi-use drug delivery device 1300 according to the present disclosure, wherein the main portion 310 comprises a central channel portion 1355 comprising a proximal flow channel in a central support structure, and radial channel outlets 312 (one on each side). The proximal flow channel is in fluid communication with the reservoir 311 (not shown). The main portion 310 further comprises a movable valve member 1340, sliding on a radial surface of the central channel portion and adapted to be positioned in a normally closed distal position wherein the outlets 312 are closed and an open proximal position, wherein the outlets 312 are positioned in the outlet surface 314. The flow conducting device 360 comprises a receiving portion 1370 adapted to receive the central channel portion 1255 with the outlets 312, and thereby form the combined flow path 302. The receiving portion 1370 further comprises receiving channels adapted to form fluid tight pressure seals with surrounding the outlets 312. FIG. 13A illustrates the drug delivery device in the connected configuration. FIG. 13B illustrates the drug delivery device in the intermediate configuration. FIG. 13C illustrates the drug delivery device in the unconnected configuration. When the drug delivery device is changed from the connected to the unconnected it will enter an intermediate configuration, in analogy to the illustrated embodiments in FIGS. 5-9.

In the illustrated embodiments of FIG. 10-13, the equalizing flow path 304 is defined as a flow path from an equalizing inlet 305 in fluid communication with the external environment, along the outlet surface 314 and to the fluid communication volume 301, and wherein the intermediate configuration further comprises the equalizing inlet is adapted to be in equilibrium with the channel outlet. The intermediate configuration for the drug delivery device 1000 is not specifically illustrated. Alternatively, the equalizing flow could be provided from an internal pressure chamber (not illustrated).

In the illustrated embodiments of FIG. 10-13, the outlet surface 314 of the main portion further comprises a first sealing portion 1015, 1115, 1215, 1315. The inlet surface 368 of the flow conducting device further comprises a second sealing portion 1069, 1169, 1269, 1369 adapted to provide a pressure seal 1007, 1107, 1207, 1307 with the first sealing portion, in response to the establishment of a compression force between the two sealing portions, wherein the pressure seal provides a portion of the combined flow path established in the connected configuration.

In the illustrated embodiments of FIG. 10-13, the connected configuration further comprises the pressure seal 1007, 1107, 1207, 1307 adapted to sustain an internal fluid pressure in the combined channel. The intermediate configuration further comprises the pressure seal 1007, 1107, 1207, 1307 is broken and provides a portion of the equalizing flow path defined from the external environment to the fluid communication volume.

In the illustrated embodiments of FIG. 10-13, the connected configuration further comprises a gas filled state and a fluid-filled state, wherein the gas-filled state comprises the flow channel 362 is filled with air. The fluid-filled state comprises the flow channel 362 is partly filled with the fluid drug, and defines a first flow resistance for fluid flowing in the equalizing flow path 304. The equalizing flow path 304 extending from the external environment define a second flow resistance for gas flowing from the external environment to the fluid communication volume 301. The second flow resistance is smaller than the first flow resistance, whereby gas will flow along the equalizing flow path will be larger than the fluid flow along the second flow path, in response to a pressure drop in the fluid communication volume 301.

In the illustrated embodiments of FIG. 10-12, the main portion comprises a first connector 1016, 1116, 1216, wherein the flow conducting device comprises a second connector 1071, 1171, 1271, wherein the first and second connector are adapted to engage with each and provide the guided relative movement between the connected and the intermediate configuration.

In the illustrated embodiments of FIGS. 10-11, the main portion 310 is provided with a normally closed valve 1030, 1130 contributing to the pressure threshold.

Figure 14A:
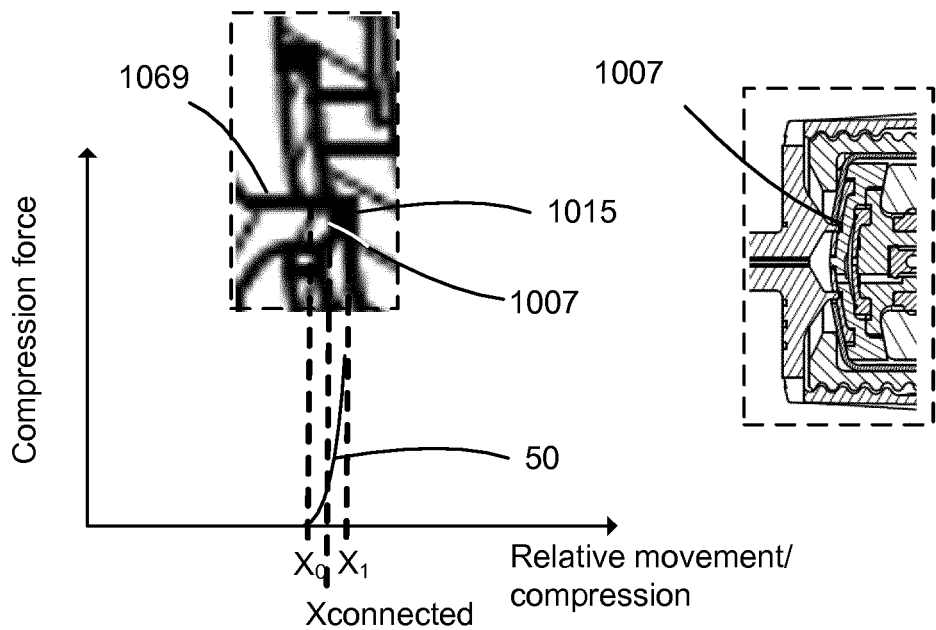
FIG. 14A illustrate the compression force as a function of the compression during the establishment of a radially extending pressure seal.
Figure 14B:
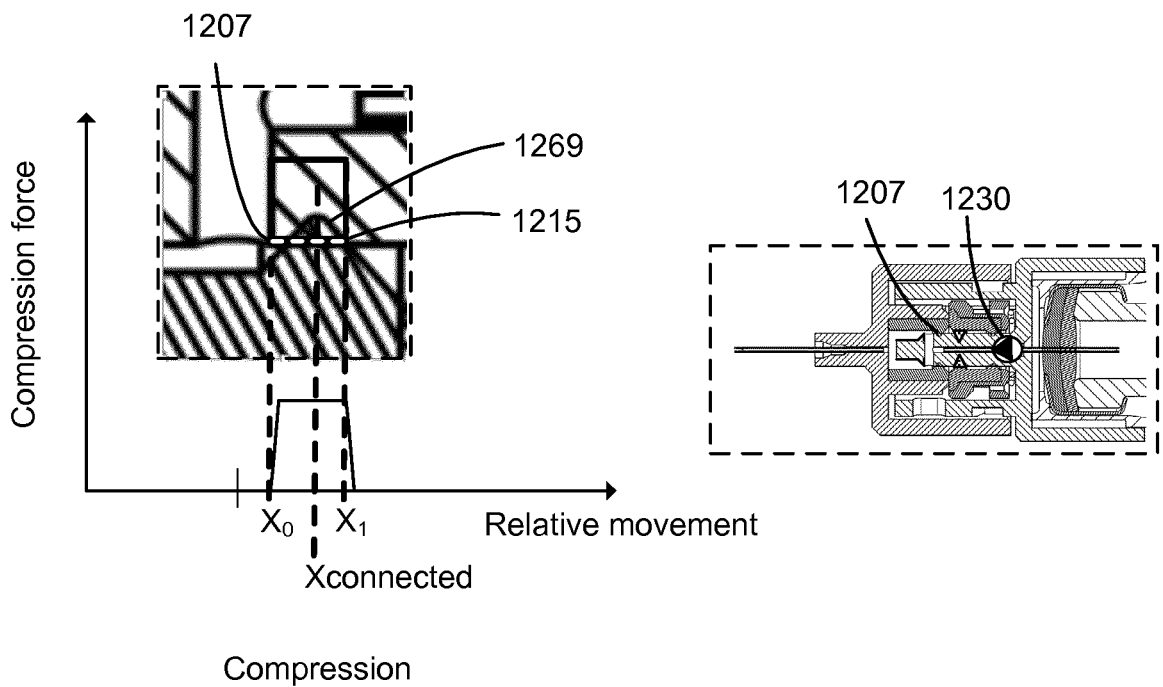
FIG. 14B illustrate the compression force as a function of the compression during the establishment of a longitudinally extending pressure seal.

In the illustrated embodiments of FIGS. 10-11, the channel seal 1007, 1107 provides a radially extending interface between the first sealing portion 1015, 1115 and the second sealing portion 1069, 1169. The channel seal can be established by moving the main portion and the flow conducting device into contact in the longitudinal direction, wherein the compression force can be increases continuously and smooth in response to movement after contact, and wherein the gradient of the compression force is continuously increasing. The radial direction is normal to the longitudinal direction, i.e., the compression force is a smooth and continuous function of the compression, which is schematically illustrated in FIG. 14A, as the compression is proportional to the relative movement for this embodiment the compression force as a function of the relative movement would have similar properties (smooth and continuous). $X_0$ illustrates a position of initial contact and $X_1$ illustrates of a position, where further compression is practically impossible. $X_{connected}$ illustrates the compression level in the connected configuration. The function 50 is only illustrative of the relation between compression and compression force or relative movement.

In the illustrated embodiment of FIG. 10, the channel outlet 1012 is provided with a normally closed valve 1030C contributing to the pressure threshold.

In the illustrated embodiment of FIG. 11, the channel outlet 312 is closed by a septum 1156 in the unconnected configuration.

In the illustrated embodiments of FIGS. 12-13, the channel seal 1207, 1307 provides a longitudinally extending interface between the first sealing portion 1215, 1315 and the second sealing portion 1269, 1369. The channel seal can be established by moving the main portion and the flow conducting device into contact in the longitudinal direction. The compression force is substantially constant in response to continued movement during contact. The radial direction is normal to the longitudinal direction. The relation between relative movement and compression force is schematically illustrated in FIG. 14A. $X_0$ illustrates a position of initial contact and $X_1$ illustrates a position, where sealing portions slides out of contact. $X_{connected}$ illustrates the compression level in the connected configuration. The function 50 is only illustrative of the relation between compression and relative movement.

In the illustrated embodiment of FIG. 13, the main portion 310 further comprises a movable valve member 1340, wherein the movable valve member is adapted for being movable in the longitudinal direction between a normally closed position, wherein the valve member closes the channel outlet 312, and a retracted open position, wherein the combined flow path 302 can be established. The valve member is adapted to be biased 2 towards the normally closed configuration, wherein the connected configuration further comprises the valve member being in the retracted open position. The intermediate configuration further comprises, the valve member being in an intermediate position between the retracted open position and the normally closed position. In the intermediate position, the fluid communication volume 301 is confined within a constant volume between the inlet surface and the outlet surface. Thereby, the fluid communication volume 301 is adapted to be substantially constant during a change between the connected and the intermediate configuration.

In a further embodiment, the present disclosure relates to a method of removing a single-use flow conducting device from a main portion of a multi-use drug delivery device 300, 400, 500, 600, 700, 800, 900, 1000, 1100, 1200, 1300 according to the present disclosure. The method comprises:
providing a multi-use drug delivery device in the connected configuration in a fluid-filled state, wherein the flow channel is partly filled with the drug from the reservoir,
removing the flow conducting device 360 by moving the flow conducting device relative to the main portion 310 and thereby changing the configuration of the drug delivery device from the connected to the unconnected configuration via the intermediate configuration, and thereby expanding the internal volume, and providing an equalizing fluid flow along the equalizing flow path 304, which is larger than an unintended flow along the unintended flow path 303, and thereby preventing a flow along the unintended flow path, and reducing the risk of introducing microorganisms from the flow channel 362 and into the reservoir 311.

LIST OF EMBODIMENTS

1. A multi-use drug delivery device (300, 400, 500, 600, 700, 800, 900, 1000, 1100, 1200, 1300) for extended use, wherein the multi-use drug delivery device comprises a multi-use main portion (310) comprising a central axis (A) defining a longitudinal direction and a single-use flow conducting device (360) adapted for conducting drug to the subcutaneous tissue of a subject, wherein the drug delivery device is adapted to enable the flow conducting device to be movably arranged relative to the main portion, wherein the relative movement can be guided by cooperating structures of the main portion and the flow conducting device, wherein the drug delivery device is configurable in:
a connected configuration, wherein the flow conducting device (360) is arranged in a connected position relative to the main portion (310), wherein the relative movement is guided, and wherein the relative position defines a first distance (d1) in the longitudinal direction between the flow conducting device and the main portion, wherein the relative position corresponds to a first internal volume confined by an outer surface (306) of the drug delivery device (300),
an intermediate configuration, wherein the flow conducting device (360) is movably arranged in an intermediate position relative to the main portion (310), wherein the relative movement is guided, and wherein the relative position defines a second distance (d2) in the longitudinal direction between the flow conducting device and the main portion, which is larger than the first distance (d1), wherein the relative position corresponds to a second internal volume confined by an outer surface (306) of the drug delivery device (300),
an unconnected configuration, wherein the flow conducting device (360) is arranged in an unconnected position relative to the main portion (310), wherein the relative movement is not guided, and thereby the main portion and the flow conducting device are not connected, and
wherein a change of configuration of the drug delivery device is adapted to be provided by a movement of the flow conducting device in the longitudinal direction relative to the main portion (310), wherein the change from the connected configuration to the unconnected configuration is through the intermediate configuration,
wherein the second internal volume is larger than the first internal volume, and whereby the internal volume confined by the outer surface (306) of the drug delivery device expands, in response to changing the drug delivery device from the connected configuration to the intermediate configuration,
wherein the main portion (310) of the drug delivery device comprises a drug reservoir (311), a drug expelling mechanism for pressurizing the reservoir and thereby expelling an amount of drug, wherein the reservoir comprises multiple doses of a liquid drug formulation, and wherein the drug formulation allows microbial growth upon introduction of microorganisms into the reservoir during extended use,
wherein the main portion (310) further comprises a drug outlet (312) and an outlet surface (314), wherein the outlet surface provides a portion of an outer surface of the main portion, and
wherein the flow conducting device (360) comprises a flow channel (362) comprising a channel inlet (364) and a channel outlet (366), wherein the flow channel is adapted for forming a combined flow path (302) with the drug outlet (312), wherein the flow conducting device (360) further comprises an inlet surface (368) for interfacing the outlet surface (314) of the main portion, wherein the drug delivery device further defines a fluid communication volume (301) being a fluid or gaseous volume at the channel inlet (364), and an unintended flow path (303) from the channel outlet (366) through the flow channel (362) and to the fluid communication volume (301), and wherein the connected configuration further comprises, the outlet surface (314) is interfacing the inlet surface (368), and wherein the drug outlet (312) is arranged in the outlet surface (314) to allow the drug to flow from the main portion to the flow conducting device along the combined flow path (302), in response to the pressure in the reservoir exceeds a pressure threshold, and wherein the fluid communication volume provides a portion of the combined flow path and the first internal volume of the drug delivery device (300), and wherein the unconnected configuration further comprises, the outlet surface is exposed to the external environment, the drug outlet is arranged in a closed state, and wherein the drug outlet is arranged to inhibit the introduction of microorganisms from the external environment and into the reservoir, wherein the intermediate configuration further comprises an equalizing channel defining an equalizing flow path (304) different from the unintended flow path (303), wherein the equalizing channel defining the equalizing flow path (304) is adapted for equalizing the fluid pressure in the fluid communication volume (301) to the fluid pressure at the channel outlet (366), upon changing the configuration from the connected to the intermediate configuration and thereby expanding the internal volume, whereby an equalizing fluid flow along the equalizing flow path is larger than an unintended flow along the unintended flow path, whereby equalization of the fluid communication volume is provided with a reduced risk of introducing microorganisms from the flow channel (362) into the reservoir (311).

2. A multi-use drug delivery device (300, 400, 500, 600, 700, 800, 900, 1000, 1100, 1200, 1300) according to embodiment 1, wherein the equalizing flow path (304) is defined as a flow path from an equalizing inlet (305) in fluid communication with the external environment, along the outlet surface (314) and to the fluid communication volume (301), and wherein the intermediate configuration further comprises the equalizing inlet is adapted to be in equilibrium with the channel outlet.

3. A multi-use drug delivery device (300, 400, 500, 600, 700, 800, 900, 1000, 1100, 1200, 1300) according to any of the previous embodiments, wherein the outlet surface (314) of the main portion further comprises a first sealing portion (1015, 1115, 1215, 1315), and wherein the inlet surface (368) of the flow conducting device further comprises a second sealing portion (1069, 1169, 1269, 1369) adapted to provide a pressure seal (1007, 1107, 1207, 1307) with the first sealing portion, in response to the establishment of a compression force between the two sealing portions, wherein the pressure seal provides a portion of the combined flow path established in the connected configuration.

4. A multi-use drug delivery device (300, 400, 500, 600, 700, 800, 900, 1000, 1100, 1200, 1300) according to embodiment 3, wherein the connected configuration further comprises the pressure seal (1007, 1107, 1207, 1307) is adapted to sustain an internal fluid pressure in the combined channel, wherein the intermediate configuration further comprises the pressure seal (1007, 1107, 1207, 1307) is broken and provides a portion of the equalizing flow path defined from the external environment to the fluid communication volume.

5. A multi-use drug delivery device (300, 400, 1000, 1100) according to any of the embodiments 3-4, wherein the channel seal (1007, 1107) provides a radially extending interface between the first sealing portion (1015, 1115) and the second sealing portion (1069, 1169), wherein the channel seal can be established by moving the main portion and the flow conducting device into contact in the longitudinal direction, wherein the compression force can be increases continuously in response to movement after contact, and wherein the gradient of the compression force is continuously increasing, and wherein the radial direction is normal to the longitudinal direction.

6. A multi-use drug delivery device (500, 600, 700, 800, 900, 1200, 1300) according to any of the embodiments 3-4, wherein the channel seal (1207, 1307) provides a longitudinally extending interface between the first sealing portion (1215, 1315) and the second sealing portion (1269, 1369), wherein the channel seal can be established by moving the main portion and the flow conducting device into contact in the longitudinal direction, wherein the compression force is substantially constant in response to continued movement during contact, and wherein the radial direction is normal to the longitudinal direction.

7. A multi-use drug delivery device (1300) according to embodiment 6, wherein the main portion (310) further comprises a movable valve member (1340), wherein the movable valve member is adapted for being movable in the longitudinal direction between a normally closed position, wherein the valve member closes the channel outlet (312), and a retracted open position, wherein the combined flow path (302) can be established, and wherein the valve member is adapted to be biased towards the normally closed configuration, wherein the connected configuration further comprises the valve member being in the retracted open position, wherein the intermediate configuration further comprises, the valve member being in an intermediate position between the retracted open position and the normally closed position, wherein the fluid communication volume (301) is confined between the inlet surface and the outlet surface within a constant volume, and whereby the fluid communication volume (301) is adapted to be substantially constant during a change between the connected and the intermediate configuration.

8 A multi-use drug delivery device (300, 400, 500, 600, 700, 800, 900, 1000, 1100, 1200, 1300) according to any of the previous embodiments, wherein the connected configuration further comprises a gas filled state and a fluid-filled state, wherein the gas-filled state comprises the flow channel (362) is filled with air, and wherein the fluid-filled state comprises the flow channel (362) is partly filled with the fluid drug, and defines a first flow resistance for fluid flowing in the equalizing flow path (304), wherein the equalizing flow path (304) from the external environment define a second flow resistance for gas flowing from the external environment to the fluid communication volume (301), wherein the second flow resistance is smaller than the first flow resistance, whereby gas will flow along the equalizing flow path will be larger than the fluid flow along the second flow path, in response to a pressure drop in the fluid communication volume (301).

9. A multi-use drug delivery device (300, 400, 500, 600, 700, 800, 900, 1000, 1100, 1200, 1300) according to any of the previous embodiments, wherein the main portion comprises a first connector (1016, 1116, 1216), wherein the flow conducting device comprises a second connector (1071, 1171, 1271), wherein the first and second connector are adapted to engage with each and provide the guided relative movement between the connected and the intermediate configuration.

10. A multi-use drug delivery device (300, 400, 500, 600, 700, 800, 900, 1000, 1100, 1200, 1300) according to any of the previous embodiments, wherein the main portion (310) is provided with a normally closed valve (1030) contributing to the pressure threshold.

11. A multi-use drug delivery device (300, 400, 1000) according to any of the previous embodiments, wherein the channel outlet (1012) is provided with a normally closed valve (1030C) contributing to the pressure threshold.

12. A multi-use drug delivery device (1200) according to any of the embodiments 1-9, wherein the channel outlet (312) is closed by a septum in the unconnected configuration.

13. A method of removing a single-use flow conducting device from a main portion of a multi-use drug delivery device (300, 400, 500, 600, 700, 800, 900, 1000, 1100, 1200, 1300) according to any of the previous embodiments, wherein the method comprises:
   providing a multi-use drug delivery device in the connected configuration in a fluid-filled state, wherein the flow channel is partly filled with the drug from the reservoir,
   removing the flow conducting device (360) by moving the flow conducting device relative to the main portion (310) and thereby changing the configuration of the drug delivery device from the connected to the unconnected configuration via the intermediate configuration, and thereby expanding the internal volume, and providing an equalizing fluid flow along the equalizing flow path (304), which is larger than an unintended flow along the unintended flow path (303), and thereby preventing a flow along the unintended flow path, and reducing the risk of introducing microorganisms from the flow channel (362) and into the reservoir (311).

The invention claimed is:

1. A multi-use drug delivery device for extended use, wherein the multi-use drug delivery device comprises a multi-use main portion comprising a central axis (A) defining a longitudinal direction and a single-use flow conducting device adapted for conducting drug to subcutaneous tissue of a subject, wherein the drug delivery device is adapted to enable the flow conducting device to be movably arranged relative to the main portion, wherein the relative movement can be guided by cooperating structures of the main portion and the flow conducting device, wherein the drug delivery device is configurable in:
   a connected configuration, wherein the flow conducting device is arranged in a connected position relative to the main portion, wherein the relative movement is guided, and wherein the relative position defines a first distance (d1) in the longitudinal direction between the flow conducting device and the main portion, wherein the relative position corresponds to a first internal volume confined by an outer surface of the drug delivery device,
   an intermediate configuration, wherein the flow conducting device is movably arranged in an intermediate position relative to the main portion, wherein the relative movement is guided, and wherein the relative position defines a second distance (d2) in the longitudinal direction between the flow conducting device and the main portion, which is larger than the first distance (d1), wherein the relative position corresponds to a second internal volume confined by an outer surface of the drug delivery device,
   an unconnected configuration, wherein the flow conducting device is arranged in an unconnected position relative to the main portion, wherein the relative movement is not guided, and thereby the main portion and the flow conducting device are not connected, and
   wherein a change of configuration of the drug delivery device is adapted to be provided by a movement of the flow conducting device in the longitudinal direction relative to the main portion, wherein the change from the connected configuration to the unconnected configuration is through the intermediate configuration,
wherein the second internal volume is larger than the first internal volume, and whereby the internal volume which transitions from the first internal volume to the second internal volume and confined by the outer surface of the drug delivery device expands, in response to changing the drug delivery device from the connected configuration to the intermediate configuration,
   wherein the main portion of the drug delivery device comprises a drug reservoir, a drug expelling mechanism for pressurizing the reservoir and thereby expelling an amount of drug, wherein the reservoir comprises multiple doses of a liquid drug formulation, and wherein the drug formulation allows microbial growth upon introduction of microorganisms into the reservoir during extended use,
wherein the main portion further comprises a drug outlet and an outlet surface, wherein the outlet surface provides a portion of an outer surface of the main portion, and
   wherein the flow conducting device comprises a flow channel comprising a channel inlet and a channel outlet, wherein the flow channel is adapted for forming a combined flow path with the drug outlet,
wherein the flow conducting device further comprises an inlet surface for interfacing the outlet surface of the main portion,
   wherein the drug delivery device further defines a fluid communication volume being a fluid or gaseous volume at the channel inlet, and an unintended flow path from the channel outlet through the flow channel and to the fluid communication volume, and
   wherein the connected configuration further comprises, the outlet surface is interfacing the inlet surface, and wherein the drug outlet is arranged in the outlet surface to allow the drug to flow from the main portion to the flow conducting device along the combined flow path, in response to the pressure in the reservoir exceeding a pressure threshold, and wherein the fluid communication volume provides a portion of the combined flow path and the first internal volume of the drug delivery device, and wherein the unconnected configuration further comprises, the outlet surface is exposed to the external environment, the drug outlet is arranged in a closed state, and wherein the drug outlet is arranged to inhibit the introduction of microorganisms from the external environment and into the reservoir, wherein the intermediate configuration further comprises an equalizing channel defining an equalizing flow path different from the unintended flow path, wherein the equalizing channel defining the equalizing flow path is adapted for equalizing the fluid pressure in the fluid communication volume to the fluid pressure at the channel outlet, upon changing the configuration from the connected to the intermediate configuration and thereby expanding an internal volume which transitions from the first internal volume to the second internal volume, whereby an equalizing fluid flow along the equalizing flow path is larger than an unintended flow along the unintended flow path, whereby equalization of the fluid communication volume is provided with a reduced risk of introducing microorganisms from the flow channel into the reservoir.

2. A multi-use drug delivery device according to claim 1, wherein the equalizing flow path is defined as a flow path from an equalizing inlet in fluid communication with the external environment, along the outlet surface and to the fluid communication volume, and wherein the intermediate configuration further comprises the equalizing inlet is adapted to be in equilibrium with the channel outlet.

3. A multi-use drug delivery device according to claim 1, wherein the outlet surface of the main portion further comprises a first sealing portion, and wherein the inlet surface of the flow conducting device further comprises a second sealing portion adapted to provide a pressure seal with the first sealing portion, in response to the establishment of a compression force between the two sealing portions, wherein the pressure seal provides a portion of the combined flow path established in the connected configuration.

4. A multi-use drug delivery device according to claim 3, wherein the connected configuration further comprises the pressure seal is adapted to sustain an internal fluid pressure in the combined channel, wherein the intermediate configuration further comprises the pressure seal is broken and provides a portion of the equalizing flow path defined from the external environment to the fluid communication volume.

5. A multi-use drug delivery device according to claim 3, wherein the channel seal provides a radially extending interface between the first sealing portion and the second sealing portion, wherein the channel seal can be established by moving the main portion and the flow conducting device into contact in the longitudinal direction, wherein the compression force can be increased continuously in response to movement after contact, and wherein the gradient of the compression force is continuously increasing, and wherein the radial direction is normal to the longitudinal direction.

6. A multi-use drug delivery device according to claim 3, wherein the channel seal provides a longitudinally extending interface between the first sealing portion and the second sealing portion, wherein the channel seal can be established by moving the main portion and the flow conducting device into contact in the longitudinal direction, wherein the compression force is substantially constant in response to continued movement during contact, and wherein the radial direction is normal to the longitudinal direction.

7. A multi-use drug delivery device according to claim 6, wherein the main portion further comprises a movable valve member, wherein the movable valve member is adapted for being movable in the longitudinal direction between a normally closed position, wherein the valve member closes the channel outlet, and a retracted open position, wherein the combined flow path can be established, and wherein the valve member is adapted to be biased towards the normally closed configuration, wherein the connected configuration further comprises the valve member being in the retracted open position, wherein the intermediate configuration further comprises, the valve member being in an intermediate position between the retracted open position and the normally closed position, wherein the fluid communication volume is confined between the inlet surface and the outlet surface within a constant volume, and whereby the fluid communication volume is adapted to be substantially constant during a change between the connected and the intermediate configuration.

8. A multi-use drug delivery device according to claim 1, wherein the connected configuration further comprises a gas filled state and a fluid-filled state, wherein the gas-filled state comprises the flow channel is filled with air, and wherein the fluid-filled state comprises the flow channel is partly filled with the fluid drug, and defines a first flow resistance for fluid flowing in the flow channel, wherein the equalizing flow path from the external environment define a second flow path having a second flow resistance for gas flowing from the external environment to the fluid communication volume, wherein the second flow resistance is smaller than the first flow resistance, whereby the gas flow along the equalizing flow path will be larger than the fluid flow along the second flow path, in response to a pressure drop in the fluid communication volume.

9. A multi-use drug delivery device according to claim 1, wherein the main portion comprises a first connector, wherein the flow conducting device comprises a second connector, wherein the first and second connector are adapted to engage with each and provide the guided relative movement between the connected and the intermediate configuration.

10. A multi-use drug delivery device according to claim 1, wherein the main portion is provided with a normally closed valve contributing to the pressure threshold.

11. A multi-use drug delivery device according to claim 1, wherein the channel outlet is provided with a normally closed valve contributing to the pressure threshold.

12. A multi-use drug delivery device according to claim 1, wherein the channel outlet is closed by a septum in the unconnected configuration.

13. A method of removing a single-use flow conducting device from a main portion of a multi-use drug delivery device according to claim 1, wherein the method comprises:

providing a multi-use drug delivery device in the connected configuration in a fluid-filled state, wherein the flow channel is partly filled with the drug from the reservoir, removing the flow conducting device by moving the flow conducting device relative to the main portion and thereby changing the configuration of the drug delivery device from the connected to the unconnected configuration via the intermediate configuration, and thereby expanding the internal volume, and providing an equalizing fluid flow along the equalizing flow path, which is larger than an unintended flow along the unintended flow path, and thereby preventing a flow along the unintended flow path, and reducing the risk of introducing microorganisms from the flow channel and into the reservoir.

14. A multi-use drug delivery device according to claim 1, wherein the drug reservoir further comprises a cartridge, wherein the cartridge comprises a distal opening closed by a needle pierceable septum.

15. A multi-use drug delivery device according to claim 14, wherein the main portion comprises a needle, wherein, for the drug delivery device being in the connected configuration, the needle pierces the pierceable septum to allow the drug to flow from the main portion to the flow conducting device along the combined flow path, in response to the pressure in the reservoir exceeds a pressure threshold.

* * * * *